(12) United States Patent
Plakogiannis et al.

(10) Patent No.: US 12,268,699 B2
(45) Date of Patent: *Apr. 8, 2025

(54) TRANSDERMAL DELIVERY OF TETRAHYDROCANNABINOL

(71) Applicant: Pike Therapeutics Inc., Vancouver (CA)

(72) Inventors: Fotios M. Plakogiannis, Whitestone, NY (US); Tamanna Lather, Jersey City, NJ (US); Nisarg Modi, Jersey City, NJ (US); Marina Borovinskaya, East Brunswick, NJ (US)

(73) Assignee: Pike Therapeutics Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/773,898

(22) Filed: Jul. 16, 2024

(65) Prior Publication Data
US 2025/0009768 A1 Jan. 9, 2025

Related U.S. Application Data

(63) Continuation-in-part of application No. 17/069,181, filed on Oct. 13, 2020, now Pat. No. 12,097,293.

(60) Provisional application No. 62/914,662, filed on Oct. 14, 2019.

(51) Int. Cl.
| | | |
|---|---|---|
| A61K 31/00 | (2006.01) | |
| A61K 9/70 | (2006.01) | |
| A61K 47/02 | (2006.01) | |
| A61K 47/10 | (2017.01) | |
| A61K 47/12 | (2006.01) | |
| A61K 47/32 | (2006.01) | |

(52) U.S. Cl.
CPC .......... A61K 31/658 (2023.05); A61K 9/7084 (2013.01); A61K 47/02 (2013.01); A61K 47/10 (2013.01); A61K 47/12 (2013.01); A61K 47/32 (2013.01)

(58) Field of Classification Search
CPC .... A61K 31/658; A61K 9/7084; A61K 47/02; A61K 47/10; A61K 47/12; A61K 47/32
See application file for complete search history.

(56) References Cited

U.S. PATENT DOCUMENTS

| | | | |
|---|---|---|---|
| 6,113,940 A | 9/2000 | Brooke et al. | |
| 6,245,347 B1 | 6/2001 | Zhang et al. | |
| 6,946,150 B2 | 9/2005 | Whittle | |
| 7,025,992 B2 | 4/2006 | Whittle et al. | |
| 7,423,026 B2 | 9/2008 | Järvinen et al. | |
| 7,544,676 B2 | 6/2009 | Dolle et al. | |
| 7,592,328 B2 | 9/2009 | Jarho et al. | |
| 7,622,140 B2 | 11/2009 | Whittle et al. | |
| 7,671,052 B2 | 3/2010 | Dolle et al. | |
| 7,709,536 B2 | 5/2010 | Whittle | |
| 7,807,711 B2 | 10/2010 | Korthout et al. | |
| 7,968,594 B2 | 6/2011 | Guy et al. | |
| 8,071,641 B2 | 12/2011 | Weiss et al. | |
| 8,071,642 B2 | 12/2011 | Laskin et al. | |
| 8,211,946 B2 | 7/2012 | Whittle | |
| 8,246,981 B2 | 8/2012 | Patel et al. | |
| 8,293,786 B2 | 10/2012 | Stinchcomb et al. | |
| 8,435,556 B2 | 5/2013 | Stinchcomb et al. | |
| 8,449,908 B2 | 5/2013 | Stinchcomb et al. | |
| 8,481,085 B2 | 7/2013 | Musty et al. | |
| 8,603,515 B2 | 12/2013 | Whittle | |
| 8,642,645 B2 | 2/2014 | Kelly | |
| 8,771,760 B2 | 7/2014 | Guy et al. | |
| 8,992,908 B2 | 3/2015 | Smith et al. | |
| 9,029,423 B2 | 5/2015 | Whittle | |
| 9,034,395 B2 | 5/2015 | Whittle et al. | |
| 9,205,063 B2 | 12/2015 | Guy et al. | |
| 9,304,134 B2 | 4/2016 | Smith | |
| 9,375,417 B2 | 6/2016 | Smith et al. | |
| 9,533,942 B2 | 1/2017 | Stinchcomb et al. | |
| 9,603,887 B2 | 3/2017 | Kelly | |
| 9,763,912 B2 | 9/2017 | Chen et al. | |
| 9,833,433 B1 | 12/2017 | Chen et al. | |
| 9,918,961 B2 | 3/2018 | Hearn et al. | |
| 9,949,937 B2 | 4/2018 | Guy et al. | |
| 9,956,183 B2 | 5/2018 | Guy et al. | |
| 9,956,184 B2 | 5/2018 | Guy et al. | |
| 9,956,185 B2 | 5/2018 | Guy et al. | |
| 9,956,186 B2 | 5/2018 | Guy et al. | |
| 9,957,321 B2 | 5/2018 | Smith et al. | |
| 9,962,340 B2 | 5/2018 | Weimann | |

(Continued)

FOREIGN PATENT DOCUMENTS

| | | |
|---|---|---|
| CA | 2859930 A1 | 3/2016 |
| JP | 2012525416 A | 10/2012 |

(Continued)

OTHER PUBLICATIONS

Office Action for Australian Patent Application No. 2020366147 issued on Jun. 19, 2024.

(Continued)

*Primary Examiner* — Trevor Love
(74) *Attorney, Agent, or Firm* — Potomac Law Group, PLLC; Joseph F. Murphy

(57) ABSTRACT

Provided is a transdermal drug delivery system comprising tetrahydrocannabinol (THC). Transdermal delivery can provide a drug plasma concentration at predetermined rate for a predetermined period of time with a simplified therapeutic regimen by decreasing dosing frequency for the treatment and/or prevention of pain and/or inflammation.

21 Claims, No Drawings

(56) References Cited

U.S. PATENT DOCUMENTS

| | | |
|---|---|---|
| 9,962,341 B2 | 5/2018 | Stott et al. |
| 10,004,684 B2 | 6/2018 | Whittle et al. |
| 10,028,904 B2 | 7/2018 | Smith et al. |
| 10,028,994 B2 | 7/2018 | Perricone |
| 10,092,525 B2 | 10/2018 | Guy et al. |
| 10,098,867 B2 | 10/2018 | Javid et al. |
| 10,098,895 B2 | 10/2018 | Chang et al. |
| 10,111,840 B2 | 10/2018 | Guy et al. |
| 10,118,006 B2 | 11/2018 | Davidson et al. |
| 10,137,095 B2 | 11/2018 | Guy et al. |
| 10,155,018 B1 | 12/2018 | Jenn |
| 10,172,809 B2 | 1/2019 | Aung-Din |
| 10,195,159 B2 | 2/2019 | Whittle et al. |
| 10,213,390 B1 | 2/2019 | Bonn-Miller et al. |
| 10,272,125 B2 | 4/2019 | Weimann et al. |
| 10,278,996 B2 | 5/2019 | Avidov et al. |
| 10,307,392 B2 | 6/2019 | Kariman |
| 10,314,792 B2 | 6/2019 | Sebree et al. |
| 10,383,816 B2 | 8/2019 | Aung-Din |
| 10,413,521 B2 | 9/2019 | Hearn et al. |
| 10,420,809 B2 | 9/2019 | Crowley |
| 10,471,022 B2 | 11/2019 | Bonn-Miller et al. |
| 10,538,373 B2 | 1/2020 | Whittle |
| 10,555,927 B2 | 2/2020 | Jenn |
| 10,568,848 B2 | 2/2020 | Sebree et al. |
| RE47,885 E | 3/2020 | Strinchcomb et al. |
| 10,588,869 B2 | 3/2020 | Weimann |
| 10,588,871 B1 | 3/2020 | Fracassi et al. |
| 10,588,974 B2 | 3/2020 | Leone-Bay et al. |
| 10,603,288 B2 | 3/2020 | Guy et al. |
| 10,617,733 B2 | 4/2020 | Kelly |
| 10,632,064 B2 | 4/2020 | Aung-Din |
| 10,660,872 B2 | 5/2020 | Sarne |
| 10,675,240 B2 | 6/2020 | Smith et al. |
| 10,675,264 B2 | 6/2020 | Green et al. |
| 10,695,287 B2 | 6/2020 | Robbins et al. |
| 10,709,671 B2 | 7/2020 | Guy et al. |
| 10,709,673 B2 | 7/2020 | Guy |
| 10,709,674 B2 | 7/2020 | Guy et al. |
| 10,709,748 B2 | 7/2020 | Witowski et al. |
| 10,716,766 B2 | 7/2020 | Aung-Din |
| 10,751,299 B2 | 8/2020 | Ghalili |
| 10,758,497 B2 | 9/2020 | Bonn-Miller et al. |
| 10,758,514 B2 | 9/2020 | Liu et al. |
| 10,799,545 B2 | 10/2020 | Weimann |
| 10,807,777 B2 | 10/2020 | Whittle |
| 10,828,266 B2 | 11/2020 | Aung-Din |
| 10,849,860 B2 | 12/2020 | Guy et al. |
| 10,864,189 B2 | 12/2020 | Borok |
| 10,869,842 B1 | 12/2020 | Summers |
| 10,881,606 B2 | 1/2021 | Schmitz et al. |
| 10,918,608 B2 | 2/2021 | Guy et al. |
| 10,918,686 B2 | 2/2021 | Siurkus |
| 10,945,967 B2 | 3/2021 | Song |
| 10,966,939 B2 | 4/2021 | Guy et al. |
| 11,026,896 B2 | 6/2021 | Fitzsimmons et al. |
| 11,052,055 B2 | 7/2021 | Kochinke |
| 11,065,209 B2 | 7/2021 | Guy et al. |
| 11,065,227 B2 | 7/2021 | Stott et al. |
| 11,096,905 B2 | 8/2021 | Guy et al. |
| 11,116,730 B2 | 9/2021 | Fracassi et al. |
| 11,147,799 B2 | 10/2021 | Kopsky et al. |
| 11,154,516 B2 | 10/2021 | Guy et al. |
| 11,154,517 B2 | 10/2021 | Guy et al. |
| 11,160,795 B2 | 11/2021 | Guy et al. |
| 11,207,292 B2 | 12/2021 | Guy et al. |
| 2002/0019421 A1 | 2/2002 | Biberman |
| 2004/0033254 A1 | 2/2004 | Song et al. |
| 2004/0138293 A1 | 7/2004 | Werner et al. |
| 2005/0042271 A1 | 2/2005 | Xiong et al. |
| 2005/0070596 A1 | 3/2005 | Baker et al. |
| 2006/0039959 A1 | 2/2006 | Wessling |
| 2006/0135599 A1 | 6/2006 | Symonds et al. |
| 2007/0060638 A1 | 3/2007 | Olmstead et al. |
| 2007/0072939 A1 | 3/2007 | Kupper |
| 2008/0112895 A1 | 5/2008 | Kottayil et al. |
| 2009/0197941 A1 | 8/2009 | Guy et al. |
| 2009/0298929 A1 | 12/2009 | Jarho et al. |
| 2010/0035978 A1 | 2/2010 | Guy et al. |
| 2010/0168108 A1 | 7/2010 | Dolle et al. |
| 2010/0184848 A1 | 7/2010 | Wine et al. |
| 2010/0273895 A1 | 10/2010 | Stinchcomb et al. |
| 2010/0286098 A1 | 11/2010 | Robson et al. |
| 2010/0317729 A1 | 12/2010 | Guy et al. |
| 2011/0021617 A1 | 1/2011 | Korthout et al. |
| 2011/0052694 A1 | 3/2011 | Stinchcomb et al. |
| 2012/0034293 A1 | 2/2012 | Stinchcomb et al. |
| 2013/0022687 A1 | 1/2013 | Fitzgerald, Jr. et al. |
| 2013/0122077 A1 | 5/2013 | Al-Ghananeem |
| 2013/0245110 A1 | 9/2013 | Guy et al. |
| 2013/0253449 A1 | 9/2013 | Yoshitake et al. |
| 2014/0039043 A1 | 2/2014 | Musty et al. |
| 2014/0314757 A1 | 10/2014 | Sanchez et al. |
| 2015/0265720 A1 | 9/2015 | Levine et al. |
| 2015/0297556 A1 | 10/2015 | Smith |
| 2015/0342902 A1 | 12/2015 | Vangara et al. |
| 2015/0343071 A1 | 12/2015 | Vangara et al. |
| 2016/0000843 A1 | 1/2016 | Lowe et al. |
| 2016/0022627 A2 | 1/2016 | Smith |
| 2016/0039591 A1 | 2/2016 | Kinzer |
| 2016/0220593 A1 | 8/2016 | Anastassov et al. |
| 2016/0256411 A1 | 9/2016 | Aung-Din |
| 2016/0271252 A1 | 9/2016 | Vangara et al. |
| 2016/0338974 A1 | 11/2016 | Aung-Din |
| 2017/0042791 A1 | 2/2017 | Ghalili et al. |
| 2017/0071870 A1 | 3/2017 | Weimann |
| 2017/0202895 A1 | 7/2017 | Hugh |
| 2017/0273914 A1 | 9/2017 | Knudsen |
| 2017/0306013 A1 | 10/2017 | Clark et al. |
| 2018/0021247 A1 | 1/2018 | Ghalili et al. |
| 2018/0042845 A1 | 2/2018 | Sinai et al. |
| 2018/0049994 A1 | 2/2018 | Aung-Din |
| 2018/0071210 A1 | 3/2018 | Wilkhu et al. |
| 2018/0078512 A1 | 3/2018 | Weimann |
| 2018/0169035 A1 | 6/2018 | Eyal |
| 2018/0284402 A1 | 10/2018 | Hoag |
| 2018/0289665 A1 | 10/2018 | Turner et al. |
| 2018/0296498 A1 | 10/2018 | Kochinke |
| 2018/0311180 A1 | 11/2018 | Kochinke |
| 2018/0311181 A1 | 11/2018 | Kochinke |
| 2018/0311184 A1 | 11/2018 | Hoag |
| 2018/0318529 A1 | 11/2018 | Davidson et al. |
| 2018/0353463 A1 | 12/2018 | Winnicki |
| 2018/0360757 A1 | 12/2018 | Doroudian et al. |
| 2018/0369191 A1 | 12/2018 | Muscarella |
| 2019/0023780 A1 | 1/2019 | Smith et al. |
| 2019/0083388 A1 | 3/2019 | Gutterman et al. |
| 2019/0105298 A1 | 4/2019 | Eyal |
| 2019/0110981 A1 | 4/2019 | Weimann |
| 2019/0125779 A1 | 5/2019 | Ziburkus et al. |
| 2019/0133994 A1 | 5/2019 | Smith et al. |
| 2019/0134121 A1 | 5/2019 | Bermudez et al. |
| 2019/0167583 A1 | 6/2019 | Shah |
| 2019/0201372 A1 | 7/2019 | McKay |
| 2019/0224118 A1 | 7/2019 | Navon et al. |
| 2019/0224140 A1 | 7/2019 | Guy et al. |
| 2019/0231826 A1 | 8/2019 | Avidov et al. |
| 2019/0247453 A1 | 8/2019 | Weimann |
| 2019/0255014 A1 | 8/2019 | Gardner |
| 2019/0298683 A1 | 10/2019 | Friedman |
| 2019/0314297 A1 | 10/2019 | Gallily |
| 2019/0321355 A1 | 10/2019 | Anavi-Goffer |
| 2019/0321426 A1 | 10/2019 | Gallily |
| 2019/0328884 A1 | 10/2019 | Jones, Jr. et al. |
| 2019/0365667 A1 | 12/2019 | Wright et al. |
| 2020/0038421 A1 | 2/2020 | Anastassov et al. |
| 2020/0078332 A1 | 3/2020 | Leone-Bay et al. |
| 2020/0085816 A1 | 3/2020 | Raz |
| 2020/0093755 A1 | 3/2020 | Biro et al. |
| 2020/0108027 A1 | 4/2020 | Whalley et al. |
| 2020/0129741 A1 | 4/2020 | Kawwas et al. |
| 2020/0138771 A1 | 5/2020 | Velasco et al. |
| 2020/0138773 A1 | 5/2020 | Jenn |
| 2020/0146998 A1 | 5/2020 | Kochinke |

(56) References Cited

U.S. PATENT DOCUMENTS

| | | |
|---|---|---|
| 2020/0163980 A1 | 5/2020 | Dellinger |
| 2020/0170963 A1 | 6/2020 | Tich et al. |
| 2020/0188324 A1 | 6/2020 | Sebree et al. |
| 2020/0188348 A1 | 6/2020 | Sinai et al. |
| 2020/0206184 A1 | 7/2020 | Robson et al. |
| 2020/0214995 A1 | 7/2020 | Sebree et al. |
| 2020/0215136 A1 | 7/2020 | Naheed |
| 2020/0237683 A1 | 7/2020 | Whalley et al. |
| 2020/0253919 A1 | 8/2020 | Raz et al. |
| 2020/0261376 A1 | 8/2020 | Yu et al. |
| 2020/0261404 A1 | 8/2020 | Raz et al. |
| 2020/0276132 A1 | 9/2020 | Weimann |
| 2020/0297656 A1 | 9/2020 | Guy et al. |
| 2020/0330379 A1 | 10/2020 | Singh et al. |
| 2020/0338041 A1 | 10/2020 | Smith et al. |
| 2020/0338151 A1 | 10/2020 | Witowski et al. |
| 2020/0345653 A1 | 11/2020 | Hansen et al. |
| 2020/0345655 A1 | 11/2020 | Heinzerling et al. |
| 2020/0345657 A1 | 11/2020 | Lurya et al. |
| 2020/0345685 A1 | 11/2020 | Otiko |
| 2020/0352849 A1 | 11/2020 | Rotunda |
| 2020/0352901 A1 | 11/2020 | Raber et al. |
| 2020/0360299 A1 | 11/2020 | Bonn-Miller et al. |
| 2020/0384048 A1 | 12/2020 | Kariman |
| 2020/0384049 A1 | 12/2020 | Kariman |
| 2021/0015740 A1 | 1/2021 | Greenspan et al. |
| 2021/0015789 A1 | 1/2021 | Guy et al. |
| 2021/0023044 A1 | 1/2021 | Spirtos |
| 2021/0023045 A1 | 1/2021 | Raz et al. |
| 2021/0030777 A1 | 2/2021 | Maida |
| 2021/0052512 A1 | 2/2021 | Guy et al. |
| 2021/0052545 A1 | 2/2021 | Jones, Jr. et al. |
| 2021/0059976 A1 | 3/2021 | Wilkhu et al. |
| 2021/0069333 A1 | 3/2021 | Diez et al. |
| 2021/0077421 A1 | 3/2021 | Sebree et al. |
| 2021/0106540 A1 | 4/2021 | Plakogiannis et al. |
| 2021/0137833 A1 | 5/2021 | Wang et al. |
| 2021/0145764 A1 | 5/2021 | Lephart |
| 2021/0186860 A1 | 6/2021 | Weimann |
| 2021/0196669 A1 | 7/2021 | Schleider et al. |
| 2021/0244680 A1 | 8/2021 | Kassab et al. |
| 2021/0244683 A1 | 8/2021 | Chaiyasate |
| 2021/0244684 A1 | 8/2021 | Ghalili et al. |
| 2021/0290565 A1 | 9/2021 | Guy et al. |
| 2021/0308070 A1 | 10/2021 | Summers |
| 2021/0308072 A1 | 10/2021 | Wright et al. |
| 2021/0379011 A1 | 12/2021 | Guynn |
| 2021/0386684 A1 | 12/2021 | Weimann |
| 2021/0386685 A1 | 12/2021 | Weimann |
| 2021/0401766 A1 | 12/2021 | Rhodes et al. |
| 2021/0401770 A1 | 12/2021 | Fracassi et al. |
| 2021/0401771 A1 | 12/2021 | Guy et al. |
| 2022/0047541 A1 | 2/2022 | Plakogiannis et al. |
| 2022/0062211 A1 | 3/2022 | Stott et al. |

FOREIGN PATENT DOCUMENTS

| | | |
|---|---|---|
| WO | 0103668 A1 | 1/2001 |
| WO | 2001064149 A1 | 9/2001 |
| WO | 02064109 A2 | 8/2002 |
| WO | 02069993 A1 | 9/2002 |
| WO | 02089945 A2 | 11/2002 |
| WO | 03105800 A2 | 12/2003 |
| WO | 2004016246 A1 | 2/2004 |
| WO | 2006041841 A1 | 4/2006 |
| WO | 2006044645 A2 | 4/2006 |
| WO | 2008021394 A2 | 2/2008 |
| WO | 2008024408 A2 | 2/2008 |
| WO | 2008024490 A2 | 2/2008 |
| WO | 2008039179 A1 | 4/2008 |
| WO | 2008063625 A2 | 5/2008 |
| WO | 2009020666 A1 | 2/2009 |
| WO | 2010126501 A1 | 11/2010 |
| WO | 2011026144 | 3/2011 |
| WO | 2013108254 A1 | 7/2013 |
| WO | 2015025312 A1 | 2/2015 |
| WO | 2018071581 A1 | 4/2018 |
| WO | 2018135943 A1 | 7/2018 |
| WO | 2019052303 A1 | 3/2019 |
| WO | 2019056123 A1 | 3/2019 |
| WO | 2019130215 A1 | 7/2019 |
| WO | 2019140321 A1 | 7/2019 |
| WO | 2019210287 A1 | 10/2019 |
| WO | 2020016581 A1 | 1/2020 |
| WO | 2020016582 A1 | 1/2020 |
| WO | 2020053857 A1 | 3/2020 |
| WO | 20200142692 A1 | 5/2020 |
| WO | 2020115751 A1 | 6/2020 |
| WO | 2020123625 A1 | 6/2020 |
| WO | 2020136593 A1 | 7/2020 |
| WO | 2020136627 A1 | 7/2020 |
| WO | 2020152438 A1 | 7/2020 |
| WO | 2020157569 A1 | 8/2020 |
| WO | 2020157639 A1 | 8/2020 |
| WO | 2020181295 A1 | 9/2020 |
| WO | 2020183350 A1 | 9/2020 |
| WO | 2020198252 A1 | 10/2020 |
| WO | 2020198883 A1 | 10/2020 |
| WO | 2020220092 A1 | 11/2020 |
| WO | 2021003341 A1 | 1/2021 |
| WO | 2021003467 A1 | 1/2021 |
| WO | 2021023351 A1 | 2/2021 |
| WO | 2021050429 A1 | 3/2021 |
| WO | 2021055499 A1 | 3/2021 |
| WO | 2021074790 A1 | 4/2021 |
| WO | 2021102353 A1 | 5/2021 |
| WO | 2021177937 A1 | 9/2021 |
| WO | 2021177940 A1 | 9/2021 |
| WO | 2021214545 A1 | 10/2021 |
| WO | 2021236782 A1 | 11/2021 |
| WO | 2022003623 A1 | 1/2022 |
| WO | 2022118303 A1 | 6/2022 |

OTHER PUBLICATIONS

Office Action for Japanese Patent Application No. 2022-522266 issued on Sep. 26, 2024 (includes English language translation).

Alper, K. et al., "The ibogaine medical subculture", Journal of Ethnopharmacology, 2008, vol. 115, pp. 9-24.

Andersson et al., "Psychoactive substances as a last resort—a qualitative study of self-treatment of migraine and cluster headaches" Harm Reduction Journal, 2017, vol. 14, pp. 1-10.

Asi, Adhesives Transdermal Delivery Systems' 2005, retrieved from AdhesivesMag.com, Nov. 1, 2005, retrieved from Web Archive Oct. 5, 2016, https: web.archive.org/web20161005045648/https://www.adhesivesmag.com/articles/86012-adhesives-in-transdermal-drug-delivery-systems.

Beug et al., Psilocybin and Psilocin Levels In Twenty Species From Seven Genera Of Wild Mushrooms In The Pacific Northwest U.S.A., Journal of Ethnopharmacology, 1982, vol. 5, pp. 271-285.

Brown, Paul, Ph.D., Tertiary Pharmacology Review, Center For Drug Evaluation and Research: Non-Clinical Reviews; Jun. 23, 2017.

Cameron, L. et al., "Psychedelic Microdosing: Prevalence and Subjective Effects", Journal of Psychoactive Drugs, 2020, vol. 52, No. 2, pp. 113-122.

Carhart-Harris, R.L. et al., "Psilocybin with psychological support for treatment-resistant depression: six month follow-up" Psychopharmacology, 2018, 225, pp. 399-408.

Declaration of Fotios M. Plakogiannis, PhD dated May 10, 2024.

Extended European Search Report for European Application No. 20876354.00 dated Sep. 27, 2023.

Fadiman, J. et al., "Might Microdosing Psychedelics Be Safe and Beneficial? An Initial Exploration" Journal of Psychoactive Drugs, 2019, vol. 51, No. 5, pp. 118-122.

Glick, Stanley et al., "18-Methoxycoronaridine (18-MC) and Ibogaine: Comparison of Antiaddictive Effiacy Toxicity, and Mechanisms of Action" Annals of the New York Academy of Sciences, vol. 914(1), pp. 369-386.

(56) References Cited

OTHER PUBLICATIONS

Grodowska, K. et al., "Organic Solvents In The Pharmaceutical Industry", Acta Pol Pharm, Jan.-Feb. 2010, vol. 67, pp. 3-12.
International Preliminary Report on Patentability for International Application No. PCT/IB2022/053276 dated Oct. 26, 2023.
International Search Report for PCT/IB2022/053276 mailed Jul. 11, 2022.
Leehey, M. et al., "Safety and Tolerability of Cannabidiol in Parkinson Disease: An Open Label, Dose Escalation Study", Cannabis and Cannabinoid Research, Nov. 4, 2020, vol. 5, pp. 326-336.
Mcpartland, John M. et al., "Care and Feeding of the Endocannabinoid System: A Systematic Review of Potential Clinical Interventions that Upregulate the Endocannabinoid System", PLOS One, Mar. 12, 2014, vol. 9, Issue 3, pp. 1-21.
Ohlsson, Per-Ingvar, "Lactoperoxidase, a dithionite ion dismutase", Eur. J. Biochem, 1984, vol. 142, pp. 233-238.
Polito, Vince, "A systematic study of microdosing psychedelics" PLOS One, 2019, vol. 14(2) pp. 1-26.
Schalau et al., "Silicone Adhesives in Medical Applications", Applied Adhesive Bonding in Science and Technology, Edited by Halil Özer. Published: Dec. 20, 2017. DOI: 10.5772/intechopen.71817.
Shapiro, Lindsey, "Children, but Linked to Side Effects" Dravet Syndrome News, Nov. 8, 2022, https://dravetsyndromenews.com/news/cbd-prevents-seizures-dravet-children-but-tied-side-effects/.
Sinha, V.R et al., "Permeation Enhancers for Transdermal Drug Delivery", Drug Development and Industrial Pharmacy, 2000, vol. 26, pp. 1131-1140.
Smith, E. et al., "Percutaneous Penetration Enhancers" 1995, CRC Press LLC.
Syloid® Silica Excipients. Pharmaceutical and Nutraceutical Solutions. W. R. Grace & Co. 2020. https://grace.com/products/syloid-silica/.
Taylor, L et al., "A Phase I, Randomized, Double-Blind, Placebo-Controlled, Single Ascending Dose, Multiple Dose, and Food Effect Trial of the Safety, Tolerability and Pharmacokinetics of Highly Purified Cannabidiol in Healthy Subjects" CNS Drugs, 2018, 32; pp. 1053-1067.
Valenta, C et al., "The use of polymers for dermal and transdermal delivery" European Journal of Pharmaceutics and Biopharmaceutics, 2004, pp. 279-289, vol. 58.
Extended European Search Report for European Application No. 22787716.4 dated Feb. 12, 2025.

TRANSDERMAL DELIVERY OF TETRAHYDROCANNABINOL

This application is a continuation in part of U.S. Ser. No. 17/069,181 filed Oct. 13, 2020, which claims priority to U.S. Ser. No. 62/914,662 filed Oct. 14, 2019, the entireties of which are incorporated herein by reference.

BACKGROUND

Pain and Inflammation are the body's physiological responses to tissue injury, infection and genetic changes. These responses can be divided into two phases: acute and chronic. The acute phase is the early, non-specific phase and is characterized by local vasodilation, increased capillary permeability, the accumulation of fluid and blood proteins in the interstitial spaces, the migration of neutrophils out of the capillaries, and the release of inflammatory mediators. Pain is produced by all these pro-inflammatory agents, that also leads to hyperalgesia through the activation of the corresponding receptors, which are expressed by nonreceptive terminals. If the condition that causes the damage is not resolved, the inflammatory process progressed toward sub-acute/chronic inflammation, which is characterized by immunopathological changes such as the infiltration of inflammatory cells, the overexpression of pro-inflammatory genes, the dysregulation of cellular signaling and the loss of barrier function[1].

The chronic pathological pain state, including neuropathic pain, is a leading health problem worldwide as it endures beyond the resolution of the pain source and can deeply impact quality of life[2]. Unlike physiological pain, in which tissue injury and/or inflammation can induce reversible adaptive changes in the sensory nervous system leading to protective sensitization, changes in sensitivity become persistent or chronic in neuropathic pain. Furthermore, the nervous system, peripheral of central, is injured in neuropathic pain. It is characterized by pain in the absence of a noxious stimulus and may be spontaneous in its temporal characteristics or be evoked by sensory stimuli.

Arthritis is a classic example of chronic pain inflammation, as are various diseases and conditions, including, for example, cardiovascular and neurodegenerative diseases, diabetes, cancer, and asthma. Synthetic anti-inflammatory compounds are one of the general ways to control chronic inflammation and pain. There are several common side effects associated with these synthetic anti-inflammatory drug products such as gastric irritation and ulceration, renal and hepatic failure, hemolytic anemia, asthma exacerbation. Increasing amount of evidence demonstrates that the endocannabinoid system actively participates in the pathophysiology of osteoarthritis-associated joint pain. Overall, preclinical and clinical data support the potentially effective anti-inflammatory properties of endocannabinoids agonist that target CB2 (Cannabinoid receptor 2) receptors[3].

Parkinson's disease (PD) is a degenerative disorder of the central nervous system mainly affecting the motor system and belongs to a group of conditions called motor system disorders, which are the result of the loss of dopamine-producing cells in the substantia nigra. The causes of this cell death are largely unknown. Early in the course of the disease, the most obvious symptoms are movement-related; these include shaking, rigidity, slowness of movement and difficulty with walking and gait. Later, thinking and behavioral problems may arise, with dementia commonly occurring in the advanced stages of the disease. Depression is the most common psychiatric symptom. Other symptoms include sensory, sleep and emotional problems. Parkinson's disease is more common in older people, with most cases occurring after the age of 50; when it is seen in young adults, it is called Young Onset PD (YOPD). Modern treatments try to manage the early motor symptoms of Parkinson's Disease, mainly through the use of levodopa and dopamine agonists. As the disease progresses and dopamine neurons continue to be lost, a point eventually arrives at which these drugs become ineffective at treating the symptoms and at the same time produce a complication called dyskinesia, marked by involuntary writhing movements. Therefore, there is a need in the art to be able to deliver large oral equivalent dose of, for example, CBD and/or THC to obtain a therapeutic effect, and eliminate or reduce discontinuance, adverse events, and side effects, such as diarrhea, somnolence, abdominal pain, weight gain, headaches, etc., as adverse events like liver enzyme elevations, associated with large oral doses to treat motor symptoms in subjects with Parkinson's Disease, including symptoms of Parkinson's Disease as well as symptoms indirectly associated with Parkinson's Disease, such as those arising as side effects of treatment. The present disclosure provides compositions and methods for the treatment and/or prevention and/or control of Parkinson's Disease in a patient comprising administration of, for example, CBD and/or THC, as set forth herein.

*Cannabis* (marijuana) is a schedule-I drug in USA. *Cannabis* is a flowering plant which contains more than 400 phytonutrient (micronutrient). More than 100 different types of terpenoids, essential oils, antioxidants and cannabinoids have been extracted from the plant. From all of the phytochemicals, only tetrahydrocannabinol (THC) showed significant psychoactive effect. A number of research papers have been published on THC due to its psychoactive and therapeutic effects. Apart from THC, several other constituents have been studied, which also showed some therapeutic effect without psychoactive effect such as cannabidiol (CBD), cannbinol (CBN), cannabichromene (CBC), cannabigerol (CBG), tetrahydrocannbivarin (THCV), delta 9-tetrahydrocannbinol (delta9THC) and many more. It has been showed that *cannabis* and its derivatives can be used for the treatment of pain, type-2 related metabolic disorder, decrease intraocular pressure, Dravet syndrome, Lennox-Gastaut Syndrome (LGS), epilepsy, nausea, pain and wasting associated with AIDS, arthritis and rheumatism, migraines, muscle spasticity associated with multiple sclerosis and paralysis, alcohol and narcotics withdrawal, stress and depression, asthma, fibromyalgia, inflammatory pain, and pain and/or inflammation associated with chemotherapy, act as an antimicrobial. FDA approved Marinol and Syndros contains delta 9-THC, which currently used in treatment of nausea, vomiting, and anorexia associated with chemotherapy treatments. Furthermore, in April 2016 FDA gave orphan drug designation to cannabidiol for the treatment of Tuberous Sclerosis Complex (TSC), Dravet Syndrome and Lennox-Gastaut Syndrome. Cannabidiol is an orally effective treatment for pain and inflammation. (Costa, B. The non-psychoactive *cannabis* constituent cannabidiol is an orally effective therapeutic agent in rat chronic inflammatory and neuropathic pain. European Journal of Pharmacology. Volume 556, Issues 1-3, 5 Feb. 2007, Pages 75-83).

Currently, 107 different cannabinoids have been identified from *cannabis* Sativa. These compounds are similar to the endogenous cannabinoid group that consists of long chain polyunsaturated fatty acids[4]. There are two types of cannabinoid receptors: I) CB1 and II) CB2.

The endocannabinoid system is a one of the important endogenous lipids signaling pathway, which consists of cannabinoid receptors, the endogenous ligands of cannabinoid receptors (endocannabinoids) and the enzymes that regulate the biosynthesis and inactivation of endocannabinoids. The lipid signaling system is involved in many important physiological functions in the central and peripheral nervous system and in the endocrine and immune system.

These receptors are from family of Guanosine Binding Protein-Coupled Receptors, are widely expressed and distinguished by their specific function, localization and signaling mechanisms[5,3]. Cannabinoid receptor 1 (CB1), inhibits adenylate cyclase and reduce cAMP levels and protein kinase A (PKA) activity, resulting in the activation of the A-type potassium channels and decrease cellular potassium levels. This receptor mainly found in adipose tissue, the GI tract, the spinal cord, the adrenal and thyroid glands, liver, reproductive organ and immune cells[6].

Cannabidiol (CBD), a major non-psychoactive phytocannabinoid has little affinity for CB1 and CB2, and act as a partial antagonist CB1 and as a weak inverse CB2 agonist[7].

Selective CB2 agonists have shown considerable efficiency in a variety of neuropathic pain preclinical models, while increasing amounts of evidence, derived from clinical studies, have confirmed the potential of the cannabinoid system in affording benefits for patients with chronic pain and chronic inflammatory disease (arthritis). Currently, patients with chronic arthritis and musculoskeletal pain are the most prevalent users of therapeutic *cannabis* products[8].

Preclinical studies have shown that cannabinoid receptor agonists block pain in various acute and chronic pain models and that inflammation is attenuated[9-11]. Both CB1 and CB2 receptor agonists demonstrate anti-nociceptive activity, whether used singly or in combination, with CB2 activity believed to affect microglial cells and thereby reduce neuro-inflammatory mechanisms[12,13]. The CB2 receptor is thought to be particularly important in central neuronal pain circuits, as agonist activity induces dopamine release in mid-brain areas, contributing to descending pain control and the placebo effect[14]. Inflammatory effects can either be modulated via the upregulation of cannabinoid receptor activity or increased production of endocannabinoids, providing an attenuation in joint destruction in preclinical models of inflammatory arthritis that mimic human rheumatoid arthritis[8,10]. Similarly, CB1 and CB2 receptors, proteins and endocannabinoids are found in the human synovial tissue of patients with both rheumatoid arthritis and osteoarthritis[15].

It was demonstrated that transdermal CBD delivery has therapeutic potential for the relief of arthritic pain-related behavior and to exert an anti-inflammatory effect without any evident of psychoactive effect using complete Freund's adjuvant-induced monoarthritic knee join mode. Result also showed that a dose of 6.2 mg/day reduce knee-joint swelling and that increase the dose of 62 mg/day failed to yield any additional improvement[16].

Many orally delivered drugs irritate the gastrointestinal mucosa and a large number, including CBD and/or THC, undergo extensive 'first-pass' inactivation by the liver. The compositions and methods of the disclosure are directed to drug delivery directly to the systemic circulation via application to the skin, and thus the compositions and methods of the disclosure overcome these problems because the active agent avoids being metabolized by the liver after absorption, and also gastrointestinal irritation is avoided.

These side effects related to oral anti-inflammatory drugs can be avoided using transdermal route. Furthermore, the peak and valley in the plasma concentration due to oral administration can be avoided by delivering the drug molecule constantly at predetermined input rate using transdermal dosage forms.

There are numerous patents available on cannabidiol, but the utility of those patents is not evaluated. One of the examples is the U.S. Pat. No. 9,375,417B2. While the '417 patent provides some examples, there is no in-vitro or in-vivo data for those examples. Due to lack of these data, the utility is unfeasible.

U.S. Pat. No. 6,328,992 provides examples for reservoir and adhesive matrix patches. All these examples contain mixture of cannabinoids (such as delta-8-THC, delta-9-THC, cannabidiol and cannabinol) instead of cannabidiol only. The THC is an psychoactive agent and addictive substance, so, the utility of this is limited.

There is a need for an improved drug delivery system of cannabidiol which can overcome the drawbacks associated with oral routes. Transdermal delivery of cannabidiol, the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, active metabolites thereof, alone or in combinations thereof can address the challenges associated with oral drug delivery. The current disclosure addresses all the above drawbacks and provide patent which can have a real world utility. Furthermore, the current disclosure provides for the use of a synthetic version of cannabidiol which is manufactured in more controlled environment than the botanical source of the same. In addition, the synthetic version of cannabidiol can provide more permeability as compared to adulterated version of it.

Moreover, the disclosure is directed to, for example, transdermal matrix patches which can deliver synthetic cannabidiol for 1 day, and/or 2-days, and/or 3-days, and/or 4 days, and/or 5 days, and/or 6 days, and/or 7 days, and/or up to 15 days.

All references cited herein are incorporated herein by reference in their entireties.

BRIEF SUMMARY

In Transdermal drug delivery, a transdermal patch or transdermal composition is applied topically to the skin surface. Throughout the duration of topical application of a transdermal patch or transdermal composition drug is continuously released and delivered through the intact skin (via transcellular, intercellular and transappendageal routes) to achieve systemic effect. Therefore, once applied transdermal composition or transdermal patch can deliver drug into systemic circulation throughout the day or even for more than one day depending on the duration of its application which can be even up to a week.

Transdermal delivery can reduce the dosing frequency of cannabidiol, tetrahydrocannabinol, the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, active metabolites thereof, alone or in combinations thereof. Through transdermal delivery, transdermal compositions or transdermal formulations or transdermal patch of cannabidiol, tetrahydrocannabinol, the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, active metabolites thereof, alone or in combinations thereof, can be applied topically to skin thereby delivering the drug throughout the duration of topical application. Depending on the requirement, the duration of topical application can be once in a day, once in two days, once in three days, once in four days, once in five days, once in a week. Therefore, transdermal delivery can overcome the multiple dose regimen of oral delivery by reducing the dosing frequency.

Moreover, in transdermal drug delivery the drug is delivered slowly and continuously throughout the duration of topical application hence there are no peaks and troughs in drug plasma concentration which are associated with multiple dose administration in a day. Therefore, by transdermal delivery of cannabidiol, tetrahydrocannabinol, the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, active metabolites thereof, alone or in combinations thereof, patients can have the therapeutic effect of the drug for extended period of time without drastic changes in drug plasma concentration.

When a medication is orally administered, its bioavailability generally decreases due to incomplete absorption and first-pass metabolism and may vary from patient to patient. The compositions of the disclosure overcome these problems because in transdermal delivery, active agent is delivered directly into systemic circulation through the skin, and it escapes the first pass hepatic metabolism therefore to achieve the desired therapeutic activity less drug is required, resulting into less adverse effects or side effects. Cannabinol has high lipid solubility and after oral administration undergoes hepatic first pass metabolism, therefore of the administered dose only 10%-20% reaches systemic circulation, thus as compared to oral dose, transdermal delivery a small dose of cannabidiol can give the desired therapeutic effects at a lower dose than oral. Transdermal delivery is easy, noninvasive and convenient. Administration of a transdermal patch or transdermal composition does not require medical supervision as patients can topically apply the transdermal patch or transdermal composition themselves.

Moreover, in case of any adverse effect, side effect or emergency transdermal delivery gives the liberty to terminate the therapy anytime by taking off the transdermal patch or transdermal composition from skin.

As per above stated reasons for the prevention of pain and/or inflammation transdermal delivery can provide patient friendly, simplified and convenient therapeutic regimen over traditional delivery systems. Transdermal delivery can reduce the dosing frequency of cannabidiol, the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, active metabolites thereof, alone or in combinations thereof. Depending on the necessity, dosing frequency can be once in a day, once in two days, once in three days, once in four days, once in five days, once in six days, once in a week.

Through transdermal administration of drug combination, two or more drugs can be delivered simultaneously. Depending on the necessity, dosing frequency of transdermal patch or transdermal composition containing drug combination can be once in a day, once in two days, once in three days, once in four days, once in five days, once in six days, once in a week. It would be a great addition to the patient compliance.

The disclosure provides a pharmaceutical composition comprising cannabidiol, tetrahydrocannabinol, the free base thereof, salts thereof, isomers thereof, amorphous forms thereof, crystalline forms thereof, co-crystalline forms thereof, prodrugs thereof, analogs thereof, derivatives thereof, synthetic forms thereof, biosynthetic forms thereof, active metabolites thereof, alone or in combinations thereof, in a dosage form for transdermal delivery. The disclosure provides a pharmaceutical composition comprising cannabidiol, the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, active metabolites thereof, alone or in combinations thereof in the range of 0.01%-95% w/w or w/v. The disclosure provides a pharmaceutical composition formulated as transdermal liquid formulation, transdermal semisolid formulation, or matrix patch formulation. The disclosure provides a pharmaceutical composition further comprising carriers or ingredients in effective amount selected from the group consisting of solvents, gelling agents, polymers, penetration enhancers, emollients, skin irritation reducing agents, buffering agents, pH stabilizers, solubilizers, suspending agents, dispersing agents, stabilizers, plasticizers, surfactants, antioxidants, oxidants, and combinations thereof. The disclosure provides a pharmaceutical composition further comprising carriers or ingredients in effective amount selected from the group consisting of solvents, gelling agents, polymers, penetration enhancers, emollients, skin irritation reducing agents, buffering agents, pH stabilizers, solubilizers, suspending agents, dispersing agents, stabilizers, plasticizers, surfactants, antioxidants, oxidants, fillers, pressure sensitive adhesives, and combinations thereof in the range of 0.01%-95% w/w or w/v. The disclosure provides a pharmaceutical composition wherein the carrier is present in the range of 0.01%-99.8% w/w or w/v. The disclosure provides a pharmaceutical composition which is formulated as a transdermal patch. The disclosure provides a pharmaceutical composition formulated as a transdermal patch, wherein the transdermal patch is selected from the group such as to reservoir patch, a microreservoir patch, a matrix patch, a pressure sensitive adhesive patch, extended release transdermal film a liquid reservoir system, a microreservoir patch, a matrix patch, a pressure sensitive adhesive patch, a mucoadhesive patch, and combinations thereof. The disclosure provides a pharmaceutical composition indicated for treatment of headaches, migraine, tension headaches, cluster headaches, acute pain, chronic pain, neuropathic pain, nociceptive pain, central pain, inflammatory pain, fibromyalgia, drug-induced neuropathic pain, causalgia, complex regional pain syndrome types I and II, and reflex sympathetic dystrophy (RSDS), pain and wasting associated with AIDS, arthritis and rheumatism, migraines, and muscle spasticity associated with multiple sclerosis and paralysis. The disclosure provides a pharmaceutical composition which is formulated as the transdermal formulation which can be administered in a dosage regimen selected from the group consisting of once daily, twice daily, three times a day, once in 1-8 hrs, once in 1-24 hrs, once in two days, once in three days, once in four days, once in five days, once in six days, once in a week, once in a 8 to about 13 days, once in two weeks, once in 15 days to about 30 days. The disclosure provides a pharmaceutical composition which may be formulated as microneedles. The disclosure provides a pharmaceutical composition wherein said and/or THC or derivative thereof is produced by a synthetic route or biosynthetic route.

The disclosure provides a method for the treatment and/or prevention and/or control of pain and/or inflammation comprising: selecting a patient in need of treatment and/or prevention and/or control of pain and/or inflammation; topically applying the pharmaceutical composition as disclosed herein. The disclosure provides a method for the treatment and/or prevention and/or control of pain and/or inflammation wherein the topical application of a transdermal patch for the treatment and/or prevention and/or control of pain and/or inflammation is selected from the group consisting of once in a day, once in two days, once in three days, once in four days, once in five days, once in six days, once in a week, once in ten days. The disclosure provides a method for the treatment and/or prevention and/or control of pain and/or inflammation further providing a constant rate of delivery of the active components of the transdermal patch over a time period. The disclosure provides a method for the treatment and/or prevention and/or control of pain and/or inflammation further providing a steady absorption rates of the active components of the transdermal patch over a time period. The disclosure provides a method for the treatment and/or prevention and/or control of pain and/or inflammation further achieving a constant blood serum levels of the active components of the transdermal patch over a time period. The disclosure provides a method for the treatment and/or prevention and/or control of pain and/or inflammation further achieving a reduced variability in dosage of the active components of the transdermal patches over a time period. The disclosure provides a method for the treatment and/or prevention and/or control of pain and/or inflammation further providing a plasma concentration of the active components of the transdermal patch in a therapeutic range over a period of time.

The disclosure provides a pharmaceutical composition comprising cannabidiol, tetrahydrocannabinol, the free base thereof, salts thereof, isomers thereof, amorphous forms thereof, crystalline forms thereof, co-crystalline forms thereof, prodrugs thereof, analogs thereof, derivatives thereof, synthetic forms thereof, biosynthetic forms thereof, active metabolites thereof, alone or in combinations thereof, in a dosage form for transdermal delivery. The disclosure provides a pharmaceutical composition comprising cannabidiol, the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, active metabolites thereof, alone or in combinations thereof in the range of 0.01%-95% w/w or w/v. The disclosure provides a pharmaceutical composition formulated as transdermal liquid formulation, transdermal semisolid formulation, or matrix patch formulation. The disclosure provides a pharmaceutical composition further comprising carriers or ingredients in effective amount selected from the group consisting of solvents, gelling agents, polymers, penetration enhancers, emollients, skin irritation reducing agents, buffering agents, pH stabilizers, solubilizers, suspending agents, dispersing agents, stabilizers, plasticizers, surfactants, antioxidants, oxidants, fillers, pressure sensitive adhesives, and combinations thereof. The disclosure provides a pharmaceutical composition further comprising carriers or ingredients in effective amount selected from the group consisting of solvents, gelling agents, polymers, penetration enhancers, emollients, skin irritation reducing agents, buffering agents, pH stabilizers, solubilizers, suspending agents, dispersing agents, stabilizers, plasticizers, surfactants, antioxidants, oxidants, fillers, pressure sensitive adhesives, and combinations thereof in the range of 0.01%-95% w/w or w/v. The disclosure provides a pharmaceutical composition wherein the carrier is present in the range of 0.01%-99.8% w/w or w/v. The disclosure provides a pharmaceutical composition which is formulated as a transdermal patch. The disclosure provides a pharmaceutical composition formulated as a transdermal patch, wherein the transdermal patch is selected from the group such as to reservoir patch, a microreservoir patch, a liquid reservoir system, a microreservoir patch, a matrix patch, a pressure sensitive adhesive patch, a mucoadhesive patch, and combinations thereof, transdermal matrix patch without any limitations such as adhesive matrix patch, non-adhesive matrix patch, pressure sensitive adhesive matrix patch, extended release transdermal films, drug in adhesive matrix patch. The disclosure provides a pharmaceutical composition indicated for treatment of conditions selected from the group consisting of headaches, migraine, tension headaches, cluster headaches, acute pain, chronic pain, neuropathic pain, nociceptive pain, central pain, inflammatory pain, fibromyalgia, drug-induced neuropathic pain, causalgia, complex regional pain syndrome types I and II, and reflex sympathetic dystrophy (RSDS), pain and wasting associated with AIDS, arthritis and rheumatism, migraines, and muscle spasticity associated with multiple sclerosis and paralysis, Autism Spectrum Disorder (ASD) and Autism Spectrum Disorder (ASD) for Pediatric patients, pain and/or inflammation of patients with liver disease, pain and/or inflammation of patients with kidney disease, pain and/or inflammation for liver cancer patients, treating pain and/or inflammation for kidney cancer patients, pain and/or inflammation for cancer patients, and combinations thereof. The disclosure provides a pharmaceutical composition which is formulated as the transdermal formulation is applied to the patient for a time selected from the group consisting of, for example, about 4 hours, 8 hours, 12 hours, 16 hours, 24 hours, 48 hours, 60 hours, 72 hours, 84 hours, 108 hours, 120 hours, one day, two days, three days, four days, five days, 6 days, 7 days, 8 days, 9 days, 10 days, 11 days, 12, days, 13, days, 14 days, one week, two weeks, three weeks, four weeks, one month, two months, three months, and four months. The disclosure provides a pharmaceutical composition which may be formulated as microneedles. The disclosure provides a pharmaceutical composition wherein said CBD and/or THC or derivative thereof is produced by a synthetic route or biosynthetic route.

The disclosure provides a pharmaceutical composition comprising cannabidiol (CBD) and/or tetrahydrocannabinol (THC), in a dosage form for transdermal delivery wherein the pharmaceutical composition comprises: about 9% to about 12% w/w of CBD and/or THC; optionally, about 30% to about 99% solvent; optionally, about 1% to about 20% penetration enhancer(s), wherein the pH of the composition is maintained at approximately 4.0 to 8.0. The disclosure provides a pharmaceutical composition formulated as transdermal liquid formulation, transdermal semisolid formulation, or transdermal polymer matrix formulation. The disclosure provides a pharmaceutical composition further comprising carriers or ingredients in effective amount selected from the group consisting of gelling agents, polymers, emollients, skin irritation reducing agents, buffering agents, pH stabilizers, solubilizers, suspending agents, dispersing agents, stabilizers, plasticizers, surfactants, antioxidants, oxidants, and combinations thereof. The disclosure provides a pharmaceutical composition further comprising carriers or ingredients in effective amount selected from the group consisting of gelling agents, polymers, emollients, skin irritation reducing agents, buffering agents, pH stabilizers, solubilizers, suspending agents, dispersing agents, stabilizers, plasticizers, surfactants, antioxidants, oxidants, and combinations thereof in the range of 0.01%-95% w/w or w/v. The disclosure provides a pharmaceutical composition which is formulated as a transdermal patch. The disclosure provides a pharmaceutical composition formulated as a transdermal patch, wherein the transdermal patch is selected from the group such as to reservoir patch, a microreservoir patch, a matrix patch, a pressure sensitive adhesive patch, extended release transdermal film a liquid reservoir system, a microreservoir patch, a matrix patch, a pressure sensitive adhesive patch, a mucoadhesive patch, and combinations thereof. The disclosure provides a pharmaceutical composition which is formulated as the transdermal formulation which can be administered in a dosage regimen selected from the group consisting of once daily, twice daily, three times a day, once in 1-8 hrs, once in 1-24 hrs, once in two days, once in three days, once in four days, once in five days, once in six days, once in a week, once in a 8 to about 13 days, once in two weeks, once in 15 days to about 30 days. The disclosure provides a pharmaceutical composition which may be formulated as microneedles. The disclosure provides a pharmaceutical composition wherein said CBD and/or THC or derivative thereof is produced by a synthetic route.

The disclosure provides a method for the treatment and/or prevention and/or decrease and/or control of pain and/or inflammation comprising: selecting a patient in need of treatment and/or prevention and/or control of pain and/or inflammation; topically applying the pharmaceutical composition as disclosed herein. The disclosure provides a method for the treatment and/or prevention and/or control of pain and/or inflammation wherein the topical application of a transdermal patch for the treatment and/or prevention and/or control of pain and/or inflammation is selected from the group consisting of once in a day, once in two days, once in three days, once in four days, once in five days, once in six days, once in a week, once in ten days. The disclosure provides a method for the treatment and/or prevention and/or control of pain and/or inflammation further providing a constant rate of delivery of the active components of the transdermal patch over a time period. The disclosure provides a method for the treatment and/or prevention and/or control of pain and/or inflammation further providing a steady absorption rates of the active components of the transdermal patch over a time period. The disclosure provides a method for the treatment and/or prevention and/or control of pain and/or inflammation further achieving a constant blood serum levels of the active components of the transdermal patch over a time period. The disclosure provides a method for the treatment and/or prevention and/or control of pain and/or inflammation further achieving a reduced variability in dosage of the active components of the transdermal patches over a time period. The disclosure provides a method for the treatment and/or prevention and/or control of pain and/or inflammation further providing a plasma concentration of the active components of the transdermal patch in a therapeutic range over a period of time. The disclosure provides a method for the treatment and/or prevention and/or control of pain and/or inflammation wherein the topical application of a transdermal patch is for the treatment and/or prevention and/or control of pain and/or inflammation of indications selected from the group consisting of headaches, migraine, tension headaches, cluster headaches, acute pain, chronic pain, neuropathic pain, nociceptive pain, central pain, inflammatory pain, fibromyalgia, drug-induced neuropathic pain, causalgia, complex regional pain syndrome types I and II, and reflex sympathetic dystrophy (RSDS), pain and wasting associated with AIDS, arthritis and rheumatism, migraines, and muscle spasticity associated with multiple sclerosis and paralysis, Autism Spectrum Disorder (ASD) and Autism Spectrum Disorder (ASD) for Pediatric patients, pain and/or inflammation of patients with liver disease, pain and/or inflammation of patients with kidney disease, pain and/or inflammation for liver cancer patients, treating pain and/or inflammation for kidney cancer patients, pain and/or inflammation for cancer patients, and combinations thereof.

The disclosure provides a transdermal and/or topical pharmaceutical composition comprising: about 0.1% to about 20% of an active agent selected from the group consisting of synthetic cannabidiol, natural cannabidiol, and combinations thereof; about 35% to about 99% of at least one adhesive and/or polymer; optionally about 0.1% to about 30% of at least one penetration enhancer; optionally about 0.1% to about 40% of a gelling agent. The disclosure provides a transdermal and/or topical pharmaceutical composition wherein said CBD and/or THC or derivative thereof is produced by a synthetic route. The disclosure provides a transdermal and/or topical pharmaceutical composition wherein the active agent is a highly purified extract of *cannabis* which comprises at least about 90% (w/w) cannabidiol (CBD) and/or THC. The disclosure provides a transdermal and/or topical pharmaceutical composition wherein the adhesive and/or polymer is selected from the group consisting of hydroxylpropylmethyl cellulose, synthetic polymers and its derivatives, carboxyvinyl polymers or carbomers, carbopol 940, carbopol 934, carbopol 971p NF, polyethylene, and its co-polymers, clays, silicates, bentonite, silicon dioxide, polyvinyl alcohol, acrylic polymers, eudragit, acrylic acid esters, polyacrylate copolymers, polyacrylamide, polyvinyl pyrrolidone homopolymer and polyvinyl pyrrolidone copolymers, PVP, Kollidon 30, poloxamer, PVPK-30, PVPK-90, isobutylene, ethyl vinyl acetate copolymers, natural rubber, synthetic rubber, pressure sensitive adhesives, bio psa 4302, bio-psa 4501, 4202, acrylic pressure sensitive adhesives, duro-tak 87-2156, duro-tak 387-2287, polyisobutylene, polyisobutylene low molecular weight, polyisobutylene medium molecular weight, polyisobutylene 35000 mw, acrylic copolymers, rubber based adhesives, hot melt adhesives, styrene-butadiene copolymers, bentonite, all water and/or organic solvent swellable polymers, and combinations thereof. The disclosure provides a transdermal and/or topical pharmaceutical composition wherein the at least one penetration enhancer is present and is selected from the group consisting of dimethylsulfoxide, dimethylacetamide, dimethylformamide, decymethylsulfoxide, dimethylisosorbide, 1,3-butanediol, azone, pyrrolidones, N-methyl-2-pyrrolidone, 2-pyrrolidon, esters, fatty acid esters, propylene glycol monolaurate, butyl ethanoate, ethyl ethanoate, isopropyl myristate, isopropyl palmitate, methyl ethanoate, decyl oleate, glycerol monooleate, glycerol monolaurate, methyl laurate, lauryl laurate, fatty acids, capric acid, caprylic acid, lauric acid, oleic acid, myristic acid, linoleic acid, stearic acid, palmitic acid, alcohols, fatty alcohols and glycols, oleyl alcohol, nathanol, dodecanol, propylene glycol, glycerol, ether alcohol, diethylene glycol monoethyl ether, urea, triglycerides, triacetin, polyoxyethylene fatty alcohol ethers, polyoxyethylene fatty acid esters, esters of fatty alcohols, essential oils, surfactant type enhancers, brij, sodium lauryl sulfate, tween, polysorbate, terpene, terpenoids and combinations thereof. The disclosure provides a transdermal and/or topical pharmaceutical composition wherein the at least one gelling agent is present and is selected from the group consisting of natural polymers, polysaccharides and its derivatives, agar, alginic acid and derivatives, *cassia* tora, collagen, gelatin, gellum gum, guar gum, pectin, potassium or sodium carrageenan, tragacanth, xanthum gum, copal, starch, chitosan, resin, synthetic polymers and its derivatives, carboxyvinyl polymers or carbomers, carbopol 940, carbopol 934, carbopol 971, polyethylene and its co-polymers, clays, silicate, polyvinyl alcohol, polyacrylamide, polyvinyl pyrrolidone homopolymer and polyvinyl pyyrolidone copolymers, PVP, Poloxamer, PVPK-30, PVPK-90, acrylic acid its ester, polyacrylate copolymers, isobutylene, ethylene vinyl acetate copolymers, natural rubbers, synthetic rubbers such as styrene-diene copolymers, styrene-butadiene block copolymers, isoprene block copolymers, acrylonitrile butadiene rubber, butyl rubber or neoprene rubber, pressure sensitive adhesive based on silicone, hot-melt adhesive, and combinations thereof. The disclosure provides a transdermal and/or topical pharmaceutical composition further comprising carriers or ingredients in effective amount selected from the group consisting of solvents, emollients, skin irritation reducing agents, buffering agents, pH stabilizers, solubilizers, suspending agents, dispersing agents, stabilizers, plasticizers, surfactants, antioxidants, oxidants, and combinations thereof. The disclosure provides a transdermal and/or topical pharmaceutical composition which is formulated as a transdermal patch. The disclosure provides a transdermal and/or topical pharmaceutical composition formulated as a transdermal patch, wherein the transdermal patch is selected from the group such as to reservoir patch, a microreservoir patch, a matrix patch, a pressure sensitive adhesive patch, extended-release transdermal film a liquid reservoir system, a microreservoir patch, a matrix patch, a pressure sensitive adhesive patch, a mucoadhesive patch, and combinations thereof. The disclosure provides a transdermal and/or topical pharmaceutical composition indicated for treatment of conditions selected from the group consisting of headaches, migraine, tension headaches, cluster headaches, acute pain, chronic pain, neuropathic pain, nociceptive pain, central pain, inflammatory pain, fibromyalgia, drug-induced neuropathic pain, causalgia, complex regional pain syndrome types I and II, and reflex sympathetic dystrophy (RSDS), pain and wasting associated with AIDS, arthritis and rheumatism, migraines, and muscle spasticity associated with multiple sclerosis and paralysis, Autism Spectrum Disorder (ASD) and Autism Spectrum Disorder (ASD) for Pediatric patients, pain and/or inflammation of patients with liver disease, pain and/or inflammation of patients with kidney disease, pain and/or inflammation for liver cancer patients, treating pain and/or inflammation for kidney cancer patients, pain and/or inflammation for cancer patients, and combinations thereof. The disclosure provides a transdermal and/or topical pharmaceutical composition which is formulated as the transdermal formulation is applied to the patient for a time selected from the group consisting of, for example, about 4 hours, 8 hours, 12 hours, 16 hours, 24 hours, 48 hours, 60 hours, 72 hours, 84 hours, 108 hours, 120 hours, one day, two days, three days, four days, five days, 6 days, 7 days, 8 days, 9 days, 10 days, 11 days, 12, days, 13, days, 14 days, one week, two weeks, three weeks, four weeks, one month, two months, three months, and four months. The disclosure provides a transdermal and/or topical pharmaceutical composition which may be formulated as microneedles. The disclosure provides a transdermal and/or topical pharmaceutical composition wherein said CBD and/or THC or derivative thereof is produced by a synthetic route. The disclosure provides a transdermal and/or topical pharmaceutical composition co-administered with at least one additional active agent selected from the group consisting of analgesics, anti-inflammatory agents, opioid agents, and combinations thereof. The disclosure provides a transdermal and/or topical pharmaceutical composition further comprising at least one additional active agent selected from the group consisting of analgesics, anti-inflammatory agents, opioid agents, and combinations thereof.

The disclosure provides a method for the treatment and/or prevention and/or decrease and/or control of pain and/or inflammation comprising: selecting a patient in need of treatment and/or prevention and/or decrease and/or control of pain and/or inflammation; topically applying the pharmaceutical composition as disclosed herein, thereby treating and/or preventing and/or decreasing and/or controlling pain and/or inflammation in the patient. The disclosure provides a method for the treatment and/or prevention and/or decrease and/or control of pain and/or inflammation wherein the topical application of a transdermal patch for the treatment and/or prevention and/or control of pain and/or inflammation is selected from the group consisting of once in a day, once in two days, once in three days, once in four days, once in five days, once in six days, once in a week, once in ten days, and up to 30 days. The disclosure provides a method for the treatment and/or prevention and/or decrease and/or control of pain and/or inflammation further providing a constant rate of delivery of the active components of the transdermal patch over a time period selected from the group consisting of once in a day, once in two days, once in three days, once in four days, once in five days, once in six days, once in a week, once in ten days, and up to 30 days. The disclosure provides a method for the treatment and/or prevention and/or decrease and/or control of pain and/or inflammation further providing a steady absorption rates of the active components of the transdermal patch over a time period selected from the group consisting of once in a day, once in two days, once in three days, once in four days, once in five days, once in six days, once in a week, once in ten days, and up to 30 days. The disclosure provides a method for the treatment and/or prevention and/or decrease and/or control of pain and/or inflammation further achieving a constant therapeutic blood serum levels of the active components of the transdermal patch over a time period selected from the group consisting of once in a day, once in two days, once in three days, once in four days, once in five days, once in six days, once in a week, once in ten days, and up to 30 days. The disclosure provides a method for the treatment and/or prevention and/or decrease and/or control of pain and/or inflammation further achieving a reduced variability in dosage of the active components of the transdermal patches over a time period selected from the group consisting of once in a day, once in two days, once in three days, once in four days, once in five days, once in six days, once in a week, once in ten days, and up to 30 days. The disclosure provides a method for the treatment and/or prevention and/or decrease and/or control of pain and/or inflammation further providing a therapeutic plasma concentration of the active components of the transdermal patch in a therapeutic range over a period of time selected from the group consisting of once in a day, once in two days, once in three days, once in four days, once in five days, once in six days, once in a week, once in ten days, and up to 30 days. The disclosure provides a method for the treatment and/or prevention and/or decrease and/or control of pain and/or inflammation wherein the topical application of a transdermal patch is for the treatment and/or prevention and/or control of pain and/or inflammation of indications selected from the group consisting of headaches, migraine, tension headaches, cluster headaches, acute pain, chronic pain, neuropathic pain, nociceptive pain, central pain, inflammatory pain, fibromyalgia, drug-induced neuropathic pain, causalgia, complex regional pain syndrome types I and II, and reflex sympathetic dystrophy (RSDS), pain and wasting associated with AIDS, arthritis and rheumatism, migraines, and muscle spasticity associated with multiple sclerosis and paralysis, Autism Spectrum Disorder (ASD) and Autism Spectrum Disorder (ASD) for Pediatric patients, pain and/or inflammation of patients with liver disease, pain and/or inflammation of patients with kidney disease, pain and/or inflammation for liver cancer patients, treating pain and/or inflammation for kidney cancer patients, pain and/or inflammation for cancer patients, and combinations thereof.

The disclosure provides for the use of the compositions of the invention for the production of a medicament for treating the indications as set forth herein.

In accordance with a further embodiment, the present disclosure provides a use of the pharmaceutical compositions described above, an amount effective for use in a medicament, and most preferably for use as a medicament for treating a disease or disorder in a subject.

In accordance with yet another embodiment, the present disclosure provides a use of the pharmaceutical compositions described above, and at least one additional therapeutic agent, in an amount effective for use in a medicament, and most preferably for use as a medicament for treating a disease or disorder associated with disease in a subject.

DETAILED DESCRIPTION

Cannabinoids are a group of 21-carbon-containing terpenophenolic compounds produced by *Cannabis* species. Cannabinoids may also be synthetically produced. The term "cannabinoid" refers hereinafter to a class of diverse chemical compounds that act on cannabinoid receptors on cells that repress neurotransmitter release in the brain. These receptor proteins include the endocannabinoids (produced naturally in the body by humans and animals), the phytocannabinoids (found in *cannabis* and some other plants), and synthetic cannabinoids. Lipophilic cannabinoids are generally grouped as endocannabinoids (most typically as mammalian endocannabinoids); phytocannabinoids, from plant sources; and synthetic cannabinoids. Such cannabinoids are also often classified into the following subclasses: Cannabigerols (CBG); Cannabichromenes (CBC); Cannabidiol (CBD; CBDL); Tetrahydrocannabinol (THC); Cannabinol (CBN); Cannabicyclol (CBL); Cannabielsoin (CBE); and, Cannabitriol (CBT).

Cannabidiol IUPAC Name 2-[(1R,6R)-6-isopropenyl-3-methylcyclohex-2-en-1-yl]-5-pentylbenzene-1,3-diol Chemical Formula: $C_{21}H_{30}O_2$ Molecular weight: 314.46 dalton Chemical structure is shown below as formula I Formula I

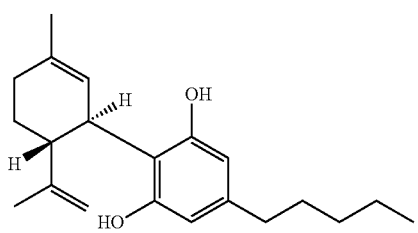

Tetrahydrocannbinol (THC) IUPAC Name (−)-(6aR,10aR)-6,6,9-Trimethyl-3-pentyl-6a,7,8,10a-tetrahydro-6H-benzo[c]chromen-1-ol Chemical Formula: $C_{21}H_{30}O_2$ Molecular weight: 314.47 dalton.

Chemical structure is shown below as formula II

Formula II

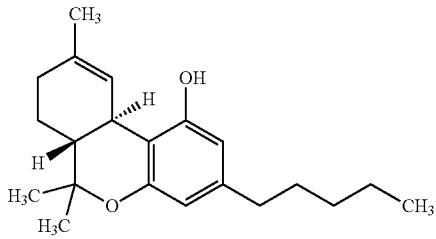

As used herein, the word *cannabis* refers to all pharmaceutically acceptable forms of *cannabis* and its derivatives either alone or in combinations thereof, for example, in following forms but not limited to such as free base or salts or isomers or amorphous or crystalline or co crystalline or solid solution or prodrugs or analogs or derivatives or metabolites. For example, cannabidiol's free base or its salts or its isomers or its amorphous form or its crystalline form or its co crystalline form or its solid solution or its prodrugs or its analogs or its derivatives or synthetic forms. The compound may be in the form of, for example, a pharmaceutically acceptable salt, such as an acid addition salt or a base salt, or a solvate thereof, including a hydrate thereof. Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts. Suitable base salts are formed from bases which form non-toxic salts and examples are the sodium, potassium, aluminium, calcium, magnesium, zinc and diethanolamine salts.

As used herein, the term "cannabidiol" includes the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, active metabolites thereof, alone or in combinations thereof. As used herein, the term "cannabidiol" includes the free base thereof, salts thereof, isomers thereof, amorphous forms thereof, crystalline forms thereof, co crystalline forms thereof, prodrugs thereof, analogs thereof, derivatives thereof, and synthetic forms thereof, alone or in combinations thereof. In certain embodiments the CBD is highly purified. In certain embodiments the CBD is present as a highly purified extract of *cannabis* which comprises at least 90%, 91%, 92%, 93%, 94%, 95%, 96%, 97%, 98%, 99%, 99.5%, or 99.75% (w/w) CBD. In exemplary embodiments, formulations of the disclosure may comprise CBD as disclosed herein at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 9.1%, about 9.2%, about 9.3%, about 9.4%, about 9.5%, about 9.6%, about 9.7%, about 9.8%, about 9.9% about 9.25%, about 9.5%, about 9.75%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise CBD at a concentration of about 1 to 25%, of about 3% to about 6%, of about 5% to about 20%, about 8% to about 15%, or about 9% to about 14%, about 9% to about 13%, about 9% to about 12%, w/w of the formulation.

In certain embodiments, the dose of CBD is greater than, for example, about 1, 2, 3, 4, 5, 6, 7, 8, 9, 10, 15, 20, 25, 30, 35, 40, or 45 mg/kg/day. In certain embodiments, the dose of CBD is greater than, for example, about 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, or 275 mg/day.

In one embodiment the CBD is present as a highly purified extract of *cannabis* which comprises at least 90%, 91%, 92%, 93%, 94%, 95%, 96%, 97%, 98%, 99%, 99.5%, or 99.75% (w/w) CBD.

As used herein, the term "tetrahydrocannabinol (THC)" includes the free base thereof, salts thereof, isomers thereof, amorphous forms thereof, crystalline forms thereof, co crystalline forms thereof, prodrugs thereof, analogs thereof, derivatives thereof, and synthetic forms thereof, alone or in combinations thereof. In certain embodiments the THC is synthetic. In certain embodiments the THC is highly purified. In certain embodiments the THC is present as a highly purified extract of *cannabis* which comprises at least 90%, 91%, 92%, 93%, 94%, 95%, 96%, 97%, 98%, 99%, 99.5%, or 99.75% (w/w) THC. In exemplary embodiments, formulations of the disclosure may comprise THC as disclosed herein at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 9.1%, about 9.2%, about 9.3%, about 9.4%, about 9.5%, about 9.6%, about 9.7%, about 9.8%, about 9.9% about 9.25%, about 9.5%, about 9.75%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise THC at a concentration of about 0.1% to about 20%, about 1 to 25%, about 3% to about 6%, about 5% to about 20%, about 8% to about 15%, or about 9% to about 14%, about 9% to about 13%, about 9% to about 12%, w/w of the formulation.

In certain embodiments, the dose of THC is greater than, for example, about 1, 2, 3, 4, 5, 6, 7, 8, 9, 10, 15, 20, 25, 30, 35, 40, or 45 mg/kg/day. In certain embodiments, the dose of THC is greater than, for example, about 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, or 275 mg/day.

As used herein, the term "pharmaceutically acceptable salts" includes acid addition salts or addition salts of free bases. The term "pharmaceutically acceptable salts" of the cannabidiol within its scope all the possible isomers and their mixtures, and any pharmaceutically acceptable metabolite, bioprecursor and/or pro-drug, such as, for example, a compound which has a structural formula different from the one of the compounds of the disclosure, and yet is directly or indirectly converted in vivo into a compound of the disclosure, upon administration to a subject, such as a mammal, particularly a human being.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is a human. As used herein, the term "agent" refers to any molecule, compound, methodology and/or substance for use in the prevention, treatment, management and/or diagnosis of a disease or condition. As used herein, the term "effective amount" refers to the amount of a therapy that is sufficient to result in the prevention of the development, recurrence, or onset of a disease or condition, and one or more symptoms thereof, to enhance or improve the prophylactic effect(s) of another therapy, reduce the severity, the duration of a disease or condition, ameliorate one or more symptoms of a disease or condition, prevent the advancement of a disease or condition, cause regression of a disease or condition, and/or enhance or improve the therapeutic effect(s) of another therapy.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the term "therapeutic agent" refers to any molecule, compound, and/or substance that is used for treating and/or managing a disease or disorder.

As used herein, the terms "therapies" and "therapy" can refer to any method(s), composition(s), and/or agent(s) that can be used in the prevention, treatment and/or management of a disease or condition, or one or more symptoms thereof. In certain embodiments, the terms "therapy" and "therapies" refer to small molecule therapy.

The term "derivative" or "derivatized" as used herein includes, for example, chemical modification of a compound of the disclosure, or extracted from botanical sources or pharmaceutically acceptable salts thereof or mixtures thereof. That is, a "derivative" may be a functional equivalent of a compound of the disclosure, which is capable of inducing the improved pharmacological functional activity in a given subject.

As used herein, the terms "composition" and "formulation" are used interchangeably.

As used herein, the terms "transdermal matrix patch" and "matrix patch" are used interchangeably.

As used herein, the term "transdermal delivery" means delivery of drug into systemic circulation through the skin.

As used herein, synthetic cannabinoids include at least the following:

AM-087 is an analgesic drug that is a cannabinoid agonist derivative of Δ8THC substituted on the 3-position side chain and a potent CB1 agonist; AM-251 is an inverse agonist at the CB1 cannabinoid receptor with close structural similarity to SR141716A (rimonabant), both of which are biarylpyrazole cannabinoid receptor antagonists as well as μ-opioid receptor antagonist; Methanandamide (AM-356) is a stable chiral analog of anandamide and acts on the cannabinoid receptors with a Ki of 17.9 nM at CB1 and 868 nM at CB2; AM-374—palmitylsulfonyl fluoride; AM-381—stearylsulfonyl fluoride; AM404, also known as N-arachidonoylaminophenol, is an active metabolite of paracetamol (acetaminophen) thought to induce its analgesic action through its activity on the endocannabinoid, COX, and TRPV systems, all of which are present in pain and thermoregulatory pathways; AM-411 is an analgesic that is a cannabinoid agonist; AM-411 is a potent and fairly selective CB1 full agonist and produces similar effects to other cannabinoid agonists such as analgesia, sedation, and anxiolysis; AM-630 (6-lodopravadoline) acts as a potent and selective inverse agonist for the cannabinoid receptor CB2, selectivity over CB1 where it acts as a weak partial agonist; AM-661—1-(N-methyl-2-piperidine)methyl-2-methyl-3-(2-iodo)benzoylindole; JWH-018 (1-pentyl-3-(1-naphthoyl) indole) or AM-678 is an analgesic chemical from the naphthoylindole family that acts as a full agonist at both the CB1 and CB2 cannabinoid receptors, with some selectivity for CB2; AM-679 acts as a moderately potent agonist for the cannabinoid receptors; AM-694 (1-(5-fluoropentyl)-3-(2-iodobenzoyl)indole) acts as a potent and selective agonist for the cannabinoid receptor CB1; AM-735—3-bornyl-Δ8-THC, a mixed CB1/CB2 agonist; AM-855 is an analgesic cannabinoid agonist at both CB1 and CB2 with moderate selectivity for CB1; AM-881—a chlorine-substituted stereoisomer of anandamide whose Ki=5.3 nM at CB1 and 95 nM at CB2; AM-883 an allyl-substituted stereoisomer of anandamide whose Ki=9.9 nM at CB1 and 226 nM at CB2; AM-905 is an analgesic cannabinoid which acts as a potent and reasonably selective agonist for the CB1 cannabinoid receptor; AM-906 is an analgesic drug which is a cannabinoid agonist and is a potent and selective agonist for the CB1 cannabinoid receptor; AM-919 is an analgesic cannabinoid receptor agonist, potent with respect to both CB1 and CB2; AM-926—a potent agonist at both CB1 and CB2 with moderate selectivity for CB1; AM-938 is an analgesic drug which is a cannabinoid receptor agonist and while it is still a potent agonist at both CB1 and CB2, it is reasonably selective for CB2; AM-1116—a dimethylated stereoisomer of anandamide; AM-1172—an endocannabinoid analog specifically designed to be a potent and selective inhibitor of AEA uptake that is resistant to FAAH hydrolysis; AM-1220 is a potent and moderately selective agonist for the cannabinoid receptor CB1; AM-1221 acts as a potent and selective agonist for the cannabinoid receptor CB2; AM-1235 (1-(5-fluoropentyl)-3-(naphthalen-1-oyl)-6-nitroindole) acts as a potent and reasonably selective agonist for the cannabinoid receptor CB1; AM-1241 (1-(methylpiperidin-2-ylmethyl)-3-(2-iodo-5-nitrobenzoyl)indole) is a potent and selective agonist for the cannabinoid receptor CB2, with analgesic effects in mammals, particularly against "atypical" pain such as hyperalgesia and allodynia, and has also shown efficacy in the treatment of amyotrophic lateral sclerosis in mammalian models; AM-1248 acts as a moderately potent agonist for both the cannabinoid receptors CB1 and CB2; AM-1710—a CB2 selective cannabilactone with 54× selectivity over CB1; AM-1714 acts as a reasonably selective agonist of the peripheral cannabinoid receptor CB2 and has both analgesic and anti-allodynia effects; AM-2201 (1-(5-fluoropentyl)-3-(1-naphthoyl)indole) acts as a potent but nonselective full agonist for the cannabinoid receptor; AM-2212—a potent agonist at both CB1 and CB2; AM-2213—a potent agonist at both CB1 and CB2; AM-2232 (1-(4-cyanobutyl)-3-(naphthalen-1-oyl)indole) acts as a potent but unselective agonist for the cannabinoid receptors CB1 and CB2; AM-2233 acts as a highly potent full agonist for the cannabinoid receptors CB1 and CB2 and has been found to fully substitute for THC in certain mammalian studies, with a potency lower than that of JWH-018 but higher than WIN 55,212-2; AM-2389 acts as a potent and reasonably selective agonist for the CB1 receptor; AM-3102—an analog of oleoylethanolamide, (the endogenous agonist for proliferator-activated receptor a (PPARα)) it acts as a weak cannabinoid agonist at CB1 and at CB2; AM-4030 an analgesic which is potent agonist at both CB1 and CB2, but also reasonably selective for CB1; AM-4054 is a potent but slow-onset agonist with CB1 affinity and selectivity CB1 over CB2; AM-4113—a CB1 selective neutral antagonist; AM-6545 acts as a peripherally selective silent antagonist for the CB1 and was developed for the treatment of obesity; JWH-007—an analgesic which acts as a cannabinoid agonist at both the CB1 receptor and CB2 receptors, with some selectivity for CB2, JWH-007 is an analgesic which acts as a cannabinoid agonist at both the CB1 and CB2 receptors; JWH-015 acts as a subtype-selective cannabinoid agonist which binds almost 28× more strongly to CB2 than CB1. and has been shown to have immunomodulatory effects, and may be useful in the treatment of pain and inflammation; JWH-018 an analgesic which acts as a full agonist at both the CB1 and CB2 cannabinoid receptors and produces effects similar to those of THC; JWH-019—an agonist at both CB1 and CB2 receptors and is an analgesic from the naphthoylindole family that acts as a cannabinoid agonist at both the CB1 and CB2 receptors; JWH-030—an analgesic which is a partial agonist at CB1 receptors; JWH-047—a potent and selective agonist for the CB2 receptor, JWH-048—a potent and selective agonist for the CB2 receptor, JWH-051—an analgesic with a high affinity for the CB1 receptor, but is a much stronger agonist for CB2, JWH-057—a 1-deoxy analog of Δ8-THC that has very high affinity for the CB2 receptor, but also has high affinity for the CB1 receptor; JWH-073—an analgesic which acts as a cannabinoid agonist at both the CB1 and CB2 receptors. It is somewhat selective for the CB1 subtype; JWH-081—an analgesic which acts as an agonist at both the cannabinoid CB1 AND CB2 receptors; JWH-098—a potent and fairly selective CB2 agonist; JWH-116—a CB1 ligand; JWH-120—a potent and 173-fold selective CB2 agonist; JWH-122—a potent and fairly selective CB1 agonist; JWH-133—a potent and highly selective CB2 receptor agonist; 1JWH-139—3-(1,1-dimethylpropyl)-6,6,9-trimethyl-6a,7,10,10a-tetrahydro-6H-benzo[c]chromene; JWH-147—an analgesic from the naphthoylpyrrole family, which acts as a cannabinoid agonist at both the CB1 and CB2 receptors; JWH-148—a moderately selective ligand for the CB2 receptor, with more than 8 times selectivity over the CB1 subtype; JWH-149—a potent and fairly selective CB2 agonist; JWH-161—a CB1 ligand; JWH-164—a potent cannabinoid agonist; JWH-166—a potent and highly selective CB2 agonist; JWH-167—a weak cannabinoid agonist from the phenylacetylindole family; JWH-171—an analgesic which acts as a cannabinoid receptor agonist; JWH-175—(1-pentylindol-3-yl)naphthalen-1-ylmethane, 22 nM at CB1, JWH-176—1-([(1E)-3-pentyliden-1-ylidine]methyl)naphthalene; JWH-181—a potent cannabinoid agonist; JWH-182—a potent cannabinoid agonist with some selectivity for CB1; JWH-184—1-pentyl-1H-indol-3-yl-(4-methyl-1-naphthyl)methane; JWH-185—1-pentyl-1H-indol-3-yl-(4-methoxy-1-naphthyl)methane; JWH-192—(1-(2-morpholin-4-ylethyl)indol-3-yl)-4-methylnaphthalen-1-ylmethane;

JWH-193—(1-(2-morpholin-4-ylethyl)indol-3-yl)-4-methylnaphthalen-1-ylmethanone; JWH-194—2-methyl-1-pentyl-1H-indol-3-yl-(4-methyl-1-naphthyl)methane; JWH-195—(1-(2-morpholin-4-ylethyl)indol-3-yl)-naphthalen-1-ylmethane; JWH-196—2-methyl-3-(1-naphthalenylmethyl)-1-pentyl-1H-Indole; JWH-197—2-methyl-1-pentyl-1H-indol-3-yl-(4-methoxy-1-naphthyl)methane; JWH-198—(1-(2-morpholin-4-ylethyl)indol-3-yl)-4-methoxynaphthalen-1-ylmethanone; JWH-199—(1-(2-morpholin-4-ylethyl)indol-3-yl)-4-methoxynaphthalen-1-ylmethane; JWH-200—an analgesic from the aminoalkylindole family, which acts as a cannabinoid receptor agonist; JWH-203—an analgesic from the phenylacetylindole family, which acts as a cannabinoid agonist with approximately equal affinity at both the CB1 and CB2 receptors; JWH-205—142-methyl-1-pentylindol-3-yl)-2-phenylethanone; JWH-210—an analgesic from the naphthoylindole family, which acts as a potent cannabinoid agonist at both the CB1 and CB2 receptors; JWH-213—a potent and fairly selective CB2 agonist; JWH-229—1-methoxy-3-(1',1'-dimethylhexyl)-Δ8-THC, a dibenzopyran cannabinoid which is a potent CB2 agonist; JWH-234—a cannabinoid agonist with selectivity for CB2; JWH-250—an analgesic from the phenylacetylindole family, which acts as a cannabinoid agonist at both the CB1 and CB2 receptors; JWH-251—(1-pentyl-3-(2-methylphenylacetyl)indole); JWH-258—a potent and mildly selective CB1 agonist; JWH-302—(1-pentyl-3-(3-methoxyphenylacetyl)indole); JWH-307—an analgesic from the naphthoylpyrrole family, which acts as a cannabinoid agonist at both the CB1 and CB2 receptors that is somewhat selective for the CB2 subtype; JWH-350—a 11-nor-1-methoxy-3-(1',1'-dimethylheptyl)-9α-hydroxyhexahydrocannabinol has a 33-fold selectivity for the CB2 receptor and high CB2receptor affinity with little affinity for the CB1 receptor; JWH-359—a dibenzopyran cannabinoid that is a potent and selective CB2 receptor agonist; JWH-387—1-pentyl-3-(4-bromo-1-naphthoyl)indole, an analgesic from the naphthoylindole family, which acts as a potent cannabinoid agonist at both receptors CB1 and CB2; JWH-398—an analgesic chemical from the naphthoylindole family, which acts as a potent cannabinoid agonist at both receptors with a Ki of 2.3 nM at CB1 and 2.8 nM at CB2; JWH-424—a potent and moderately selective CB2 agonist with a Ki of 5.44 nM at CB2 and 20.9 nM at CB1; HU-210 is a cannabinoid that is 100 to 800 times more potent than natural THC from *cannabis* and has an extended duration of action and is a ponntent analgesic with many of the same effects as natural THC; Ajulemic acid (AB-III-56, HU-239, IP-751, CPL 7075, CT-3, Resunab) is a cannabinoid derivative of the non-psychoactive THC metabolite 11-nor-9-carboxy-THC that shows useful analgesic and anti-inflammatory effects without causing a subjective "high". It is being developed for the treatment of neuropathic pain and inflammatory conditions such as arthritis and for the treatment of orphan life-threatening inflammatory diseases; HU-243 (AM-4056) is a cannabinoid which is a potent agonist at both the CB1 and CB2 receptors; HU-308 acts as a cannabinoid agonist and is highly selective for the CB2 receptor subtype. It has analgesic effects, promotes proliferation of neural stem cells, and protects both liver and blood vessel tissues against oxidative stress via inhibition of TNF-α; HU-331 is a quinone anticarcinogenic synthesized from cannabidiol; HU-336 is a strongly antiangiogenic compound, it inhibits angiogenesis by directly inducing apoptosis of vascular endothelial cells without changing the expression of pro- and anti-angiogenic cytokines and their receptors; HU-345 (cannabinol quinone) is a drug that is able to inhibit aortic ring angiogenesis more potently than its parent compound cannabinol; CP 47,497 or (C7)-CP 47,497 is a cannabinoid receptor agonist drug.

The disclosure also provides methods for the biosynthesis of cannabinoids and for the use of a eukaryotic or prokaryotic expression system for the production of biosynthetic enzymes that can be used for the manufacture of cannabinoids and cannabinoid analogs. Yeast as well as eukaryotic and prokaryotic cells are suitable for the cloning and expression of the cannabinoid acid synthase enzymes and include without limitation *E coli*, yeast and baculovirus hosts. Thus, the present disclosure provides a method for the production of biosynthetic cannabinoids, such as for example THC and/or CBD, using cannabinoid acid synthase enzymes including, but not limited to, tetrahydrocannabinolic acid (THCA) synthase and cannabidiolic acid (CBDA) synthase. The disclosure further provides for the transdermal compositions as disclosed herein comprising, for example, biosynthetic CBD and/or THC, alone or in combination with other active agents.

According to certain embodiments, transdermal compositions described herein are for the prevention and/or treatment of pain and/or inflammation. According to certain embodiments, transdermal compositions described herein are for the reduction in severity of pain and/or inflammation.

According to certain embodiments described herein, pharmaceutical composition or transdermal formulation of contains cannabidiol, the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, active metabolites thereof, alone or in combinations thereof. More preferably transdermal formulation may include cannabidiol, the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, active metabolites thereof, alone or in combinations thereof.

One embodiment of the present disclosure can be a transdermal drug delivery system which may include without any limitation to transdermal formulation, transdermal patches, topical formulation, microneedles, iontophoresis, metered dose transdermal spray.

Transdermal formulation which includes liquids for example without any limitation like solutions, suspensions, dispersions, emulsion. Transdermal formulation includes semisolids for example without any limitations like gels, ointments, emulsions, creams, suspension, paste, lotion, balm. Liquid formulation and/or gel formulation incorporated in transdermal patch is preferred. Transdermal formulations which includes matrix patch without any limitations like adhesive matrix patch, non-adhesive matrix patch, pressure sensitive adhesive matrix patch, extended release transdermal films, drug in adhesive matrix patch.

Without any limitation, transdermal patch may include all transdermal drug delivery systems stated in art preferably but not limited to reservoir patch, matrix patch, bilayer matrix patch, multilayer matrix patch, microreservoir patch, adhesive systems, transdermally applicable tape and other.

In certain embodiments of the present disclosure, a transdermal patch comprises transdermal formulation containing cannabidiol, the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, alone or in combinations thereof contained in a reservoir or a matrix, and an adhesive which allows the transdermal patch to adhere to the skin, allowing the passage of the cannabidiol, the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, active metabolites thereof, alone or in combinations thereof from the transdermal patch through the skin of the patient. The transdermal delivery system can be occlusive, semi-occlusive or non-occlusive, and can be adhesive or non-adhesive.

In certain embodiments of the present disclosure a pharmaceutical composition as disclosed herein can be co-administered with at least one additional active agent. In certain embodiments of the present disclosure a pharmaceutical composition as disclosed herein can further comprise at least one additional active agent. Examples of additional active agents include, for example, analgesics and anti-inflammatory agents, such as, aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxaprozin, oxyphenbutazone, phenylbutazone, piroxicam, sulindac; opioid analgesics, such as, codeine, dextropropoxyphene, diamorphine, dihydrocodeine, meptazinol, methadone, morphine, nalbuphine, pentazocine, midazolam, fentanyl, codeine, buprenorphine, tramadol, fentany, hydromonorphone, morphine, oxycodone/naloxone, opiate, opium, acetyldihydrocodeine, alfentani, allylprodine, alphamethylfentanyl, alphaprodine, benzylmorphine, betaprodine, bezitriamide, buprenorphine, butorphanol, bremazocine, carfentan (carfentanyl), contin, dextromoramide, dextropropoxyphene, dezocine, diacetylmorphine, diamorphine, dihydrocodeine, dihydromorphine, dihydromorphone, diphenoxylate, dipipanone, enadoline, ethylketazocine, ethylmorphine, etonitazene, etorphine, fentanyl, heroin, hydrocodone, hydromorphin (hydromorphone), hydromorphone, ketazocine, ketobemidone, lefetamine, levomethadon, levomethadyl, levomethorphan, levor-phanol, loperamide, meperidine, meptazinol, methadone, methadyl, methylmorphine, morphin (morphine), nalbuphine, narcotic, nicocodeine, nicomorphine, normorphine, noscapin, ohmefentanyl, oripavine, oxycodone, oxycontin, oxymorphone, papaveretum, papaverin, pentazocine, percocet, peronine, pethidine, phenazocine, phencyclidine, pholcodine, piritramid (priitramidine), prodine, promedol, propoxyphene, remifentanil, sufentanil, tapentadol, thebaine, tilidine, tramadol, ultracet, morphine, codeine, diyhydrocodeine, diacetylmorphine, hydrocodone, hydomorphone, levorphanol, oxymorphone, alfentanil, buprenorphine, butorphanol, fentanyl, sufentanyl, meperidine, methadone, nabulfina, propoxyphene, pentazocine and their pharmaceutically acceptable salt derivatives.

The transdermal formulation comprising cannabidiol, the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, active metabolites thereof, alone or in combinations thereof can be incorporated within the patch and patch can be applied topically to the skin surface. The patch can be left on the subject for any suitable period of time. In certain embodiments, the transdermal patch is applied to the patient for, for example, about 4 hours, 8 hours, 12 hours, 16 hours, 24 hours, 48 hours, 60 hours, 72 hours, 84 hours, 108 hours, 120 hours, one day, two days, three days, four days, five days, 6 days, 7 days, 8 days, 9 days, 10 days, 11 days, 12, days, 13, days, 14 days, one week, two weeks, three weeks, four weeks, one month, two months, three months, four months.

In some embodiments, the transdermal patches provide for a constant rate of delivery of the active components of the transdermal patch over a predetermined time period. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal patches described herein provide a steady absorption rate of the active components of the transdermal patches by the patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal patches described herein provide a constant blood serum level of the active components of the transdermal patches in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal patches described herein provide a plasma concentration of the active components of the transdermal patches in a therapeutic range in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In some embodiments the matrix patch comprising cannabidiol, the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, active metabolites thereof, alone or in combinations thereof can be prepared as transdermal matrix patch and matrix patch can be applied topically to the skin surface. The matrix patch can be left on the subject for any suitable period of time.

In some embodiments, the matrix patch provides for a constant rate of delivery of the active components of the matrix patch over a predetermined time period. In some embodiments, the predetermined time period is 24 hours, 48 hours, 72 hours, 96 hours, 120 hours, 144 hours, 7 days, 8 to 13 days, two weeks, or 15 days.

In yet further embodiments, the matrix patch described herein provide a steady absorption rate of the active components of the matrix patch by the patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the matrix patch described herein provide a constant blood serum level of the active components of the matrix patch in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the matrix patch described herein provide a plasma concentration of the active components of the matrix patch in a therapeutic range in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the matrix patch described herein allow for reduced variability in dosage of active components in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal patches described herein allow for reduced variability in dosage of active components in a patient over a predetermined time. In some embodiments, the predetermined time period is 24 hours, 48 hours, 72 hours, 96 hours, 120 hours, 144 hours, 7 days, 8 to 13 days, two weeks, or 15 days.

The topical formulation stated in the art which include, for example without any limitation, semisolids such as ointment, cream, emulsion, micro emulsion, nano emulsion, paste, balms, gels, lotions, mousses. Liquids such as solutions, suspensions, micro suspension, nano suspension, dispersions, nano dispersion etc. Sprays, aerosols, magma, etc. The topical formulation comprising cannabidiol, the free base thereof, salts thereof, isomers thereof, amorphous forms thereof, crystalline forms thereof, co crystalline forms thereof, prodrugs thereof, analogs thereof, derivatives thereof, synthetic forms thereof, biosynthetic forms thereof, active metabolites thereof, alone or in combinations thereof can be topically applied to the skin surface for transdermal delivery of cannabidiol.

The transdermal formulation and/or topical formulation of some embodiments of the present disclosure may include carriers or ingredients in effective amount either alone or in combinations thereof without any limitation to the following carriers or ingredients such as solvents, gelling agents, polymers, biodegradable polymers, penetration enhancers, emollients, skin irritation reducing agents, buffering agents, pH stabilizers, solubilizers, suspending agents, dispersing agents, stabilizers, plasticizers, tackifiers, surfactants, volatile chemicals, antioxidants, oxidants, fillers, pressure sensitive adhesives, chelating agents, complexing agents, excipients, material to prepare patch, material to prepare transdermal matrix patch, material to prepare reservoir patch etc.

Cannabidiol may be dissolved, suspended, dispersed or uniformly mixed in the above stated single carrier, mixture of carriers and combinations of carrier. Any combination of two or more drugs such as cannabidiol may be dissolved, suspended, dispersed or uniformly mixed in the above stated single carrier, mixture of carriers and combinations of carrier.

The desired optimum transdermal and/or topical formulation of cannabidiol alone or in combinations thereof may comprise without any limitation to following carriers as stated from example 1 to example 13 either alone or in combinations thereof.

The invention will be illustrated in more detail with reference to the following Examples, but it should be understood that the present invention is not deemed to be limited thereto.

EXAMPLES

Example 1

The transdermal formulation and/or topical formulation of the disclosure may comprise solvents known to those skilled in the art either alone or in combinations thereof without any limitation to following like alcohol $C_1$-$C_{20}$ such as but not limited to (methanol, ethanol, isopropyl alcohol, butanol, propanol etc.), polyhydric alcohols, glycols such as but not limited to (propylene glycol, polyethylene glycol, dipropylene glycol, hexylene glycol, butyene glycol, glycerine etc.), derivative of glycols, pyrrolidone such as but not limited to (N methyl 2-pyrrolidone, 2-pyrrolidone etc.), sulfoxides such as but not limited to (dimethyl sulfoxide, decymethylsulfoxide etc), dimethylisosorbide, mineral oils, vegetable oils, water, polar solvents, semi polar solvents, non polar solvents, volatile chemicals which can be used to make matrix patch such as but not limited to (ethanol, propanol, ethyl acetate, acetone, methanol, dichloromethane, chloroform, toluene, IPA), acids such as but not limited to acetic acid, lactic acid, levulinic acid, bases and others. More preferably in the range of 0.01%-95% w/w or w/v. In exemplary embodiments, formulations of the disclosure may comprise solvent(s) at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise solvent(s) at a concentration of about 30 to 99%, of about 35% to 95%, about 40% to about 90% w/w. In exemplary formulations of the disclosure, the solvent(s) will represent approximately 1 wt % to 75 wt %, preferably 2 wt % to 30 wt %, more preferably 5 wt. % to 20 wt. % of the formulation.

Example 2

The transdermal formulation and/or topical formulation of the disclosure may comprise gelling agents and/or thickening and/or suspending agents and/or polymers and/or pressure sensitive adhesives known to those skilled in the art either alone or in combinations thereof without any limitation to following like natural polymers, polysaccharides and its derivatives such as but not limited to (agar, alginic acid and derivatives, *cassia* tora, collagen, gelatin, gellum gum, guar gum, pectin, potassium, or sodium carageenan, tragacanth, xantham, gum copal, chitosan, resin etc.), semisynthetic polymers and its derivatives such as without any limitation to cellulose and its derivatives (methylcellulose, ethyl cellulose, carboxymethyl cellulose, hydroxylpropyl cellulose, hydroxylpropylmethyl cellulose etc.), synthetic polymers and its derivatives such as without any limitation to carboxyvinyl polymers or carbomers (carbopol 940, carbopol 934, carbopol 971p NF), polyethylene, and its copolymers etc, clays such as but not limited to (silicates, bentonite), silicon dioxide, polyvinyl alcohol, acrylic polymers (eudragit), acrylic acid esters, polyacrylate copolymers, polyacrylamide, polyvinyl pyrrolidone homopolymer and polyvinyl pyrrolidone copolymers such as but not limited to (PVP, Kollidon 30, poloxamer, PVPK-30, PVPK-90,), isobutylene, ethyl vinyl acetate copolymers, natural rubber, synthetic rubber, pressure sensitive adhesives such as without any limitation silicone polymers such as but not limited to (bio psa 4302, bio-psa 4202 etc.,), acrylic pressure sensitive adhesives such as but not limited to (duro-tak 87-2156, duro-tak 387-2287, etc.), polyisobutylene such as but not limited to (polyisobutylene low molecular weight, polyisobutylene medium molecular weight, polyisobutylene 35000 mw, etc), acrylic copolymers, rubber based adhesives, hot melt adhesives, styrene-butadiene copolymers, all water and/or organic solvent swellable polymers, etc. Polyvinyl pyrrolidone (PVP) is a water-soluble polyamide. Commercially available PVP is divided into four viscosity grades according to its K value: K-15 (average molecular weight 10,000), K-30 (average molecular weight 40,000), K-60 (average molecular weight 160,000), K-90 (average molecular weight 360,000). More preferably in the range of 0.1%-95% w/w or w/v. In exemplary embodiments, formulations of the disclosure may comprise gelling agents and/or thickening and/or suspending agents at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise gelling agents and/or thickening and/or suspending agents at a concentration of about 0.1% to about 20%, about 1 to 20%, of about 5% to 25%, about 10% to about 20%, or about 15% to about 18%, about 30% to about 70%, about 35% to about 65%, and about 40% to about 64% w/w. In exemplary formulations of the disclosure, the gelling agents and/or thickening and/or suspending agents will represent approximately 1 wt % to 75 wt %, preferably 2 wt % to 30 wt %, more preferably 5 wt. % to 20 wt. % of the formulation.

Example 3

The transdermal formulation and/or topical formulation of the disclosure may comprise penetration or permeation enhancers known to those skilled in the art either alone or in combination thereof without any limitation to the following, such as sulfoxides, and similar chemicals such as but not limited to (dimethylsulfoxide, dimethylacetamide, dimethylformamide, decymethylsulfoxide, dimethylisosorbide etc), 1,3-butanediol, azone, pyrrolidones such as but not limited to (N-methyl-2-pyrrolidone, 2-pyrrolidon etc.), esters, fatty acid esters such as but not limited to (propylene glycol monolaurate, butyl ethanoate, ethyl ethanoate, isopropyl myristate, isopropyl palmitate, methyl ethanoate, decyl oleate, glycerol monooleate, glycerol monolaurate, methyl laurate, lauryl laurate, lauryl lactate, oleyl oleate, ethyl oleate, methyl laurate, etc.), fatty acids such as but not limited to (capric acid, caprylic acid, lauric acid, oleic acid, myristic acid, linoleic acid, stearic acid, palmitic acid etc.), alcohols, fatty alcohols and glycols such as but not limited to (oleyl alcohol, nathanol, dodecanol, propylene glycol, glycerol etc.), ethers alcohol such as but not limited to (diethylene glycol monoethyl ether), urea, triglycerides such as but not limited to triacetin, polyoxyethylene fatty alcohol ethers, polyoxyethylene fatty acid esters, esters of fatty alcohols, essential oils, surfactant type enhancers such as but not limited to (brij, sodium lauryl sulfate, tween, polysorbate), terpene, terpenoids and all penetration or permeation enhancers referred in the book "Percutaneous Penetration Enhancers" (Eric W. Smith, Howard I. Maibach, 2005. November, CRC press). More preferably in the range of 0.01%-95% w/w or w/v. In exemplary embodiments, formulations of the disclosure may comprise permeation enhancer(s) at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise penetration or permeation enhancer(s) at a concentration of about 1 to 20%, of about 5% to 25%, about 10% to about 20%, or about 15% to about 18%, about 30% to about 70%, about 35% to about 65%, and about 40% to about 64% w/w. In exemplary formulations of the disclosure, the permeation enhancer(s) will represent approximately 1 wt % to 75 wt %, preferably 2 wt % to 30 wt %, more preferably 5 wt. % to 20 wt. % of the formulation.

Example 4

The transdermal formulation and/or topical formulation of the disclosure may comprise plasticizers known to those skilled in the art either alone or in combination thereof without any limitation to following like glycerol and its esters, phosphate esters, glycol derivatives, sugar alcohols, sebacic acid esters, citric acid esters, tartaric acid esters, adipate, phthalic acid esters, triacetin, oleic acid esters and all the plasticizers which can be used in transdermal drug delivery system referred in the book "Handbook of Plasticizers" (George Wypych, 2004, Chem Tec Publishing). More preferably in the range of 0.01%-95% w/w or w/v. In exemplary embodiments, formulations of the disclosure may comprise plasticizer(s) at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise plasticizer(s) at a concentration of about 1 to 20%, of about 5% to 25%, about 10% to about 20%, or about 15% to about 18%, about 30% to about 70%, about 35% to about 65%, and about 40% to about 64% w/w. In exemplary formulations of the disclosure, the plasticizer(s) will represent approximately 1 wt % to 75 wt %, preferably 2 wt % to 30 wt %, more preferably 5 wt. % to 20 wt. % of the formulation.

Example 5

The transdermal formulation and/or topical formulation of the disclosure may comprise emollients, humectants, skin irritation reducing agents and the similar compounds or chemicals known to those skilled in the art either alone or in combinations thereof without any limitation to following like petrolatum, lanolin, mineral oil, dimethicone, zinc oxide, glycerin, propylene glycol and others. More preferably in the range of 0.01%-95% w/w or w/v. In exemplary embodiments, formulations of the disclosure may comprise emollients, humectants, skin irritation reducing agents and the similar compounds or chemicals at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise emollients, humectants, skin irritation reducing agents and the similar compounds or chemicals at a concentration of about 1 to 20%, of about 5% to 25%, about 10% to about 20%, or about 15% to about 18%, about 30% to about 70%, about 35% to about 65%, and about 40% to about 64% w/w. In exemplary formulations of the disclosure, the emollients, humectants, skin irritation reducing agents and the similar compounds or chemicals will represent approximately 1 wt % to 75 wt %, preferably 2 wt % to 30 wt %, more preferably 5 wt. % to 20 wt. % of the formulation.

Example 6

The transdermal formulation and/or topical formulation of the disclosure may comprise solubilizers, surfactants, emulsifying agents, dispersing agents and similar compounds or chemicals known to those skilled in the art either alone or in combination thereof without any limitation to following like polysorbate (e.g., TWEEN®) such as but not limited to (polysorbate 20, polysorbate 40, polysorbate 60, polysorbate 80 etc.), span such as but not limited to (span 20, span 20 etc.), surfactants such as (anionic, cationic, nonionic and amphoteric), propylene glycol monocaprylate type I, propylene glycol monocaprylate type II, propylene glycol dicaprylate, medium chain triglycerides, propylene glycol monolaurate type II, linoleoyl polyoxyl-6 glycerides, oleoyl-polyoxyl-6-glycerides, lauroyl polyoxyl-6-gylcerides, ethyl oleate, polyglyceryl-3-dioleate, diethylene glycol monoethyl ether, propylene glycol monolaurate type I, polyglyceryl-3-dioleate, caprylocaproyl polyoxyl—8 glycerides etc, cyclodextrins, LABRASOL® (a caprylocaproyl macrogolglyceride, Caprylocaproyl macrogol-8 glycerides EP, Caprylocaproyl polyoxyl-8 glycerides NF), and others. More preferably in the range of 0.01% 95% w/w or w/v. In exemplary embodiments, formulations of the disclosure may comprise solubilizers, surfactants, emulsifying agents, dispersing agents and similar compounds or chemicals at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise solubilizers, surfactants, emulsifying agents, dispersing agents and similar compounds or chemicals at a concentration of about 1 to 20%, of about 5% to 25%, about 10% to about 20%, or about 15% to about 18%, about 30% to about 70%, about 35% to about 65%, and about 40% to about 64% w/w. In exemplary formulations of the disclosure, the solubilizers, surfactants, emulsifying agents, dispersing agents and similar compounds or chemicals will represent approximately 1 wt % to 75 wt %, preferably 2 wt % to 30 wt %, more preferably 5 wt. % to 20 wt. % of the formulation.

Example 7

Different techniques and ingredients can be used to increase the stability and/or solubility of cannabidiol, the free base thereof, salts thereof, isomers thereof, amorphous forms thereof, crystalline forms thereof, co-crystalline forms thereof, prodrugs thereof, analogs thereof, derivatives thereof, synthetic forms thereof, biosynthetic forms thereof, active metabolites thereof, alone or in combinations thereof in formulation such as without any limitation to coating, encapsulation, microencapsulation, nanoencapsulation, lyophilization, chelating agents, complexing agents, etc.

Example 8

The transdermal formulation and/or topical formulation of the disclosure may comprise auxiliary pH buffering agents and pH stabilizers and similar compounds known to those skilled in the art which helps to maintain the appropriate pH of formulation preferably in the range of 4.0-8.0 either alone or in combination thereof without any limitation to following such as phosphate buffer, acetate buffer, citrate buffer, etc., acids such as but not limited to (carboxylic acids, inorganic acids, sulfonic acids, vinylogous carboxylic acids and others), base such as but not limited to (sodium hydroxide, potassium hydroxide, ammonium hydroxide, triethylamine, sodium carbonate, sodium bicarbonate) etc. More preferably in the range of 0.01%-30% w/w or w/v. In exemplary embodiments, formulations of the disclosure may comprise auxiliary pH buffering agents and pH stabilizers and similar compounds at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise auxiliary pH buffering agents and pH stabilizers and similar compounds at a concentration of about 1 to 20%, of about 5% to 25%, about 10% to about 20%, or about 15% to about 18%, about 30% to about 70%, about 35% to about 65%, and about 40% to about 64% w/w. In exemplary formulations of the disclosure, the auxiliary pH buffering agents and pH stabilizers and similar compounds will represent approximately 1 wt % to 75 wt %, preferably 2 wt % to 30 wt %, more preferably 5 wt. % to 20 wt. % of the formulation. In certain embodiments, the pH of the formulation is maintained at about 4.0, about 4.5, about 5.0, about 5.5, about 6.0, about 6.5, about 7.0, about 7.5, or about 8.0. In certain embodiments, the pH of the formulation is maintained at a range of about 4.0 to about 8.0, about 4.5 to about 7.5, or about 5.0 to about 7.0.

Example 9

The transdermal formulation and/or topical formulation of the disclosure may comprise antioxidants such as but not limited to (sodium metabisulfite, citric acid, ascorbic acid, BHA, BHT), oxidizing agents, stabilizers, discoloring agents, preservatives and similar compounds or chemicals known to those skilled in the art which helps to get a stable formulation can be used either alone or in combination thereof without any limitation. More preferably in the range of 0.01%-50% w/w or w/v. In exemplary embodiments, formulations of the disclosure may comprise antioxidants at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise antioxidants at a concentration of about 1 to 20%, of about 5% to 25%, about 10% to about 20%, or about 15% to about 18%, about 30% to about 70%, about 35% to about 65%, and about 40% to about 64% w/w. In exemplary formulations of the disclosure, the antioxidants will represent approximately 1 wt % to 75 wt %, preferably 2 wt % to 30 wt %, more preferably 5 wt. % to 20 wt. % of the formulation.

Example 10

The transdermal formulation and/or topical formulation of the disclosure may be formulated in ointment and/or cream base known to those skilled in the art.

Example 11

Materials to make the transdermal delivery system of the disclosure in patch form known to those skilled in the art, for example, such as but not limited to reservoir patch, transdermal matrix patch, and may include, such as but are not limited to polymers, copolymers, derivatives, backing film, release membranes, release liners, etc. either alone or in combinations thereof. Pressure sensitive adhesives (such as but not limited to silicone polymers, rubber based adhesives, acrylic polymers, acrylic copolymers, polyisobutylene, acrylic acid-isooctyl acrylate copolymer, hot melt adhesives, polybutylene, acrylic pressure sensitive adhesives, for example, Duro-Tak 9301, Duro-Tak 2516, Duro-Tak 2207, Duro-Tak 87-2516, Duro-Tak 87-4287, Duro-Tak 87-900A, Duro-Tak 87-9301 etc.), backing film (such as but not limited to ethylene vinyl acetate copolymers, vinyl acetate resins, polyurethane, polyvinyl chloride, metal foils, polyester, aluminized films, polyethylene, light resistant backing film, etc.), release membrane (such as but not limited to microporous polyethylene membrane, microporous polypropylene membrane, rate controlling ethylene vinyl acetate copolymer membrane etc.), release liners (such as but not limited to siliconized polyester films, fluoropolymer coated polyester film, polyester film, siliconized polyethylene terephthalate film, etc.), tapes, etc.

Example 12

The transdermal formulation and/or topical formulation of the invention may comprise fillers such as but not limited to colloidal silicon dioxide, lactose, mannitol, talc, titanium dioxide, etc. clays such as but not limited to kaolin, bentonite, etc. etc. either alone or in combinations thereof. More preferably in the range of 0.01%-70% w/w or w/v.

Example 13

The transdermal formulation and/or topical formulation of the invention may comprise crystallization inhibitors, tackifiers, cross-linking agents, resins etc. either alone or in combinations thereof.

The transdermal formulation and/or topical formulation and/or transdermal delivery system of the disclosure may deliver at least therapeutic effective dose of cannabidiol, the free base thereof, salts thereof, isomers thereof, amorphous forms thereof, crystalline forms thereof, co-crystalline forms thereof, prodrugs thereof, analogs thereof, derivatives thereof, synthetic forms thereof, biosynthetic forms thereof, active metabolites thereof, alone or in combinations thereof. Therapeutic effective cannabidiol, the free base thereof, salts thereof, isomers thereof, amorphous forms thereof, crystalline forms thereof, co-crystalline forms thereof, prodrugs thereof, analogs thereof, derivatives thereof, synthetic forms thereof, biosynthetic forms thereof, active metabolites thereof, alone or in combinations thereof in human plasma required for treating and/or preventing pain and/or inflammation. Therapeutic effective cannabidiol, the free base thereof, salts thereof, isomers thereof, amorphous forms thereof, crystalline forms thereof, co-crystalline forms thereof, prodrugs thereof, analogs thereof, derivatives thereof, synthetic forms thereof, biosynthetic forms thereof, active metabolites thereof, alone or in combinations thereof dose refers to the therapeutic concentration of of these forms of cannabidiol in human plasma required for treating and/or preventing pain and/or inflammation. Furthermore, the precise therapeutic effective dose of cannabidiol, the free base thereof, salts thereof, isomers thereof, amorphous forms thereof, crystalline forms thereof, co-crystalline forms thereof, prodrugs thereof, analogs thereof, derivatives thereof, synthetic forms thereof, biosynthetic forms thereof, active metabolites thereof, alone or in combinations thereof in the transdermal formulation or topical formulation or transdermal delivery system or transdermal patch can be determined by those skilled in the art based on factors such as but not limited to the patient's condition etc. The transdermal formulation or topical formulation or transdermal delivery system or transdermal patch will be available in different dosage strengths and patch sizes in order to achieve optimum therapeutic outcome based on patient's requirement.

In yet another embodiment, the transdermal formulation and/or topical formulation and/or transdermal delivery system or transdermal patch of the disclosure may deliver at least therapeutic effective dose of cannabidiol, the free base thereof, salts thereof, isomers thereof, amorphous forms thereof, crystalline forms thereof, co-crystalline forms thereof, prodrugs thereof, analogs thereof, derivatives thereof, synthetic forms thereof, biosynthetic forms thereof, active metabolites thereof, alone or in combinations thereof. Therapeutic effective cannabidiol, the free base thereof, salts thereof, isomers thereof, amorphous forms thereof, crystalline forms thereof, co-crystalline forms thereof, prodrugs thereof, analogs thereof, derivatives thereof, synthetic forms thereof, biosynthetic forms thereof, active metabolites thereof, alone or in combinations thereof refers to the therapeutic concentration of cannabidiol, the free base thereof, salts thereof, isomers thereof, amorphous forms thereof, crystalline forms thereof, co-crystalline forms thereof, prodrugs thereof, analogs thereof, derivatives thereof, synthetic forms thereof, biosynthetic forms thereof, active metabolites thereof, alone or in combinations thereof in human plasma required for treating and/or preventing and/or controlling the conditions and/or diseases and/or disorders associated with pain: Pain syndromes include, for example, headaches, migraine, tension headaches, cluster headaches, acute pain, chronic pain, neuropathic pain, nociceptive pain, central pain, inflammatory pain, fibromyalgia, drug-induced neuropathic pain, causalgia, complex regional pain syndrome types I and II, and reflex sympathetic dystrophy (RSDS), pain and wasting associated with AIDS, arthritis and rheumatism, migraines, and muscle spasticity associated with multiple sclerosis and paralysis, Autism Spectrum Disorder (ASD), and Autism Spectrum Disorder (ASD) for Pediatric patients, pain and/or inflammation of patients with liver disease, pain and/or inflammation of patients with kidney disease, pain and/or inflammation of patients with Parkinson's Disease.

Another aspect of the present disclosure is directed to the use of the transdermal compositions as disclosed herein as a therapeutic agent for the prophylaxis and/or treatment of, for example, treating pain and/or inflammation for liver cancer patients, and to treat pain as a side effect of liver cancer medications and treatments. Another aspect of the present disclosure is directed to the use of the transdermal compositions as disclosed herein as a therapeutic agent for the prophylaxis and/or treatment of, for example, treating pain and/or inflammation for kidney cancer patients, and to treat pain as a side effect of kidney cancer medications and treatments. Another aspect of the present disclosure is directed to the use of the transdermal compositions as disclosed herein as a therapeutic agent for the prophylaxis and/or treatment of, for example, treating pain and/or inflammation for cancer patients, and to treat pain as a side effect of cancer medications and treatments.

Another aspect of the present disclosure is directed to the use of the transdermal compositions as disclosed herein as a therapeutic agent for the prophylaxis and/or treatment of, for example, immunoinflammatory disorder. The term "immunoinflammatory disorder" encompasses a variety of conditions, including autoimmune diseases, proliferative skin diseases, and inflammatory dermatoses. Immunoinflammatory disorders result in the destruction of healthy tissue by an inflammatory process, dysregulation of the immune system, and unwanted proliferation of cells. Examples of immunoinflammatory disorders are acne vulgaris; acute respiratory distress syndrome; Addison's disease; allergic rhinitis; allergic intraocular inflammatory diseases, antineutrophil cytoplasmic antibody (ANCA)-associated small-vessel vasculitis; ankylosing spondylitis; arthritis, asthma; atherosclerosis; atopic dermatitis; autoimmune hepatitis; autoimmune hemolytic anemia; autoimmune hepatitis; Behcet's disease; Bell's palsy; bullous pemphigoid; cerebral ischemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eosinophilic fasciitis; erythema nodosum; exfoliative dermatitis; fibromyalgia; focal glomerulosclerosis; focal segmental glomerulosclerosis; giant cell arteritis; gout; gouty arthritis; graft versus host disease; hand eczema; Henoch-Schonlein purpura; herpes gestationis; hirsutism; idiopathic cerato-scleritis; idiopathic pulmonary fibrosis; idiopathic thrombocytopenic purpura; immune thrombocytopenic purpura inflammatory bowel or gastrointestinal disorders, inflammatory dermatoses; lichen planus; lupus nephritis; lymphomatous tracheobronchitis; macular edema; multiple sclerosis; myasthenia gravis; myositis; non-specific fibrosing lung disease; osteoarthritis; Parkinson's Disease; pancreatitis; pemphigoid gestationis; pemphigus vulgaris; periodontitis; polyarteritis nodosa; polymyalgia rheumatica; pruritus scroti; pruritis/inflammation, psoriasis; psoriatic arthritis; pulmonary histoplasmosis; rheumatoid arthritis; relapsing polychondritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; shoulder tendinitis or bursitis; Sjogren's syndrome; Still's disease; stroke-induced brain cell death; Sweet's disease; systemic lupus erythematosus; systemic sclerosis; Takayasu's arteritis; temporal arteritis; toxic epidermal necrolysis; transplant-rejection and transplant-rejection-related syndromes; tuberculosis; type-1 diabetes; ulcerative colitis; uveitis; vasculitis; and Wegener's granulomatosis.

Another aspect of the present disclosure is directed to the use of the transdermal compositions as disclosed herein as a therapeutic agent for the prophylaxis and/or treatment of, for example, inflammation. Symptoms and signs of inflammation associated with specific conditions include: rheumatoid arthritis: pain, swelling, warmth and tenderness of the involved joints; generalized and morning stiffness; insulin-dependent diabetes mellitus-insulitis; this condition can lead to a variety of complications with an inflammatory component, including: retinopathy, neuropathy, nephropathy; coronary artery disease, peripheral vascular disease, and cerebrovascular disease; autoimmune thyroiditis: —weakness, constipation, shortness of breath, puffiness of the face, hands and feet, peripheral edema, bradycardia; multiple sclerosis: spasticity, blurry vision, vertigo, limb weakness, paresthesias; uveoretinitis: decreased night vision, loss of peripheral vision; lupus erythematosus: joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, Parkinson's Disease; pain and/or inflammation of patients with Parkinson's Disease; pericarditis; scleroderma:

Raynaud's disease; swelling of the hands, arms, legs and face; skin thickening; pain, swelling and stiffness of the fingers and knees, gastrointestinal dysfunction, restrictive lung disease; pericarditis; renal failure; other arthritic conditions having an inflammatory component such as rheumatoid spondylitis, osteoarthritis, septic arthritis and polyarthritis: fever, pain, swelling, tenderness; other inflammatory brain disorders, such as meningitis, Alzheimer's disease, AIDS dementia encephalitis: photophobia, cognitive dysfunction, memory loss; other inflammatory eye inflammations, such as retinitis: decreased visual acuity; inflammatory skin disorders, such as, eczema, other dermatites (e.g., atopic, contact), psoriasis, burns induced by UV radiation (sun rays and similar UV sources): erythema, pain, scaling, swelling, tenderness; inflammatory bowel disease, such as Crohn's disease, ulcerative colitis: pain, diarrhea, constipation, rectal bleeding, fever, arthritis; asthma: shortness of breath, wheezing; other allergy disorders, such as allergic rhinitis: sneezing, itching, runny nose conditions associated with acute trauma such as cerebral injury following stroke-sensory loss, motor loss, cognitive loss; heart tissue injury due to myocardial ischemia: pain, shortness of breath; lung injury such as that which occurs in adult respiratory distress syndrome: shortness of breath, hyperventilation, decreased oxygenation, pulmonary infiltrates; inflammation accompanying infection, such as sepsis, septic shock, toxic shock syndrome: fever, respiratory failure, tachycardia, hypotension, leukocytosis; other inflammatory conditions associated with particular organs or tissues, such as: (i) nephritis (e.g., glomeralonephritis): oliguria, abnormal urinalysis; (ii) inflamed appendix: fever, pain, tenderness, leukocytosis; (iii) gout: —pain, tenderness, swelling and erythema of the involved joint, elevated serum and/or urinary uric acid; (iv) inflamed gall bladder: —abdominal pain and tenderness, fever, nausea, leukocytosis; (v) congestive heart failure: shortness of breath, rales, peripheral edema; (vi) Type II diabetes: end organ complications including cardiovascular, ocular, renal, and peripheral vascular disease; (vii) lung (pulmonary) fibrosis: hyperventilation, shortness of breath, decreased oxygenation; (viii) vascular disease, such as atherosclerosis and restenosis: pain, loss of sensation, diminished pulses, loss of function; and (ix) alloimmunity leading to transplant rejection: pain, tenderness, fever. Another aspect of the present disclosure is directed to the use of the transdermal compositions as disclosed herein as a therapeutic agent for the prophylaxis and/or treatment of, for example, Autism Spectrum Disorder (ASD), and Autism Spectrum Disorder (ASD) for Pediatric patients.

The transdermal formulation or transdermal patch of cannabidiol, the free base thereof, salts thereof, isomers thereof, amorphous forms thereof, crystalline forms thereof, co-crystalline forms thereof, prodrugs thereof, analogs thereof, derivatives thereof, synthetic forms thereof, biosynthetic forms thereof, active metabolites thereof, alone or in combinations thereof preferably but not limited to can be applied to the skin surface in any of the following dosage regimens such as once in a day, once in two days, once in three days, once in four days, once in five days, once in six days, once in a week, once in a 8 to about 13 days, once in two weeks, once in 15 days.

Example 14

Synthetic cannabidiol (CBD) formulations for transdermal delivery ((Formulation Nos. 001, 002, 003, 004, and 005) were prepared by mixing ingredients as shown in Table 1:

TABLE 1

Transdermal Synthetic Cannabidiol formulations

| Ingredients | 001 (% W/W) | 002 (% W/W) | 003 (% W/W) | 004 (% W/W) | 005 (% W/W) |
|---|---|---|---|---|---|
| CBD | 9.35 | 9.06 | 9.34 | 9.09 | 9.13 |
| PG | 90.65 | 45.51 | 45.17 | 45.54 | 45.33 |
| Hexylene Glycol | | 45.43 | | | |
| 1,3 Butanediol | | | 45.49 | | |
| PEG-400 | | | | 45.37 | |
| Dipropylene Glycol | | | | | 45.53 |

Abbreviations: PG - propylene glycol; CBD = Cannabidiol; PEG-400: Polyethylene Glycol-400.

All of the components from Table 1, with the exception of the CBD, were mixed together with stirring for 18 hours. Next, the CBD was added into the excipient mixture to prepare the final transdermal formulations.

The prepared transdermal formulations were then subjected to a flux measurement test as follows. Human cadaver skin, stored at −80° C., was thawed at room temperature in phosphate buffered saline (PBS), and visually inspected for defects before using in the study. Transdermal flux was then measured using standard Franz diffusion cells composed of a cylindrical donor compartment and a separate water jacketed cylindrical receptor compartment with the volume of 13 mL. The human cadaver skin was clamped between the two compartments with the dermis side facing toward the receptor compartment. The donor compartment was filled with the transdermal CBD formulations prepared as described above. The receptor compartment was filled with receptor medium, held at constant temperature, and constantly stirred to collect the CBD as it diffuses through the skin and into receptor compartment. It is important to confirm that the receptor fluid is always in contact with the skin. The receptor compartment was emptied at 24 hr intervals for assay of CBD and replaced with fresh receptor solution. In order to maintain the sink condition in receptor compartment, it is important to keep the CBD concentration in receptor compartment less than 10% of its solubility. The experimental conditions are provided in Table 5:

TABLE 2

Experimental Condition for In-vitro Permeability testing

| | |
|---|---|
| Receiving Media | De-ionized water + 0.5% Brij-O(20) + 0.01% Sodium Azide |
| Receiving Media Volume (mL) | 13 |
| Sample Volume (mL) | 13 |
| Sampling Interval (hr) | 24, 48, 72, 96, 120, 144 |
| Franz-cell diffusion area (sqcm) | 1.76 |
| Membrane Type | Human Cadaver Skin |

Flux of CBD through the human cadaver skin was measured for a minimum period of 144 Hrs (6 days) and results of the flux measurement are provided in Table 6.

TABLE 3

CBD Flux Results

| | 001 | 002 | 003 | 004 | 005 |
|---|---|---|---|---|---|
| Total Amount of CBD Permeated at 144 hrs (ng/cm$^2$) | 85795 | 167045 | 150000 | 59091 | 166477 |
| Flux (ng/cm$^2$/hr) | 338.5 | 1160.03 | 1041.66 | 410.35 | 1156.09 |

Example 15

Additional synthetic Cannabidiol (CBD) formulations for transdermal delivery (Formulation Nos. 006 through 014) were prepared by mixing ingredients as shown in Table 4:

TABLE 4

Transdermal Synthetic Cannabidiol formulation no. 015 to 022

| Ingredients | 015 (% W/W) | 016 (% W/W) | 017 (% W/W) | 018 (% W/W) | 019 (% W/W) | 020 (% W/W) | 021 (% W/W) | 022 (% W/W) |
|---|---|---|---|---|---|---|---|---|
| CBD | 9.95 | 9.64 | 19.77 | 9.98 | 9.98 | 9.64 | 9.87 | 9.52 |
| PG | 42.70 | 42.58 | 42.51 | 42.51 | 42.02 | 42.45 | 42.47 | 42.34 |
| 1,3 Butanediol | 42.36 | 42.48 | 42.40 | 42.63 | 42.66 | 42.77 | 42.50 | 42.64 |
| Tween-20 | 4.99 | | | | | | | |
| Triacetin | | 5.30 | | | | | | |
| PGML | | | 5.32 | | | | | |
| OA | | | | 4.88 | | | | |
| ML | | | | | 5.34 | | | |
| IPM | | | | | | 5.16 | | |
| IPP | | | | | | | 5.04 | |
| Labrasol | | | | | | | | 4.91 |

Abbreviations: CBD = Cannabidiol; PGML: Propylene glycol monolaurate; PG = propylene glycol; OA = Oleyl Alcohol; ML = Methyl Laurate; IPM = Isopropyl Myristate; IPP: Isopropyl Palmitate.

Synthetic Cannabidiol formulations for transdermal delivery (006-014) were prepared by the same procedure described in Example 1. Flux measurement was also performed as described in Example 1. The experimental conditions are the same as provided in Table 2 of Example 1.

Flux of CBD through the human cadaver skin was measured for a minimum period of 48 Hrs and results of the flux measurement experiments are provided in Table 5.

TABLE 5

CBD Flux Results

| | Formulation No. | | | | | | | |
|---|---|---|---|---|---|---|---|---|
| | 015 | 016 | 017 | 018 | 019 | 020 | 021 | 022 |
| Total Amount of CBD Permeated at 48 hrs (ng/cm$^2$) | 25791 | 22851 | 29098 | 37085 | 37351 | 45008 | 59954 | 21524 |
| Flux (ng/cm$^2$/hr) | 537.31 | 476.06 | 606.20 | 772.60 | 778.14 | 937.67 | 1249.04 | 448.41 |

Example 16

Additional synthetic cannabidiol (CBD) formulations for transdermal delivery patches (Formulation Nos. 015 to 018) were prepared by mixing ingredients as shown in Table 6:

TABLE 6

Transdermal Synthetic cannabidiol formulation nos. 023 to 026

| Ingredients | 023 (% W/W) | 024 (% W/W) | 025 (% W/W) | 026 (% W/W) |
|---|---|---|---|---|
| CBD | 2.0 | 2.0 | 2.0 | 2.0 |
| PG | 27.8 | 27.8 | 27.8 | 27.8 |
| 1,3 Butane diol | 27.8 | 27.8 | 27.8 | 27.8 |
| Durotak 9301 | 42.4 | | | |
| Durotak 2516 | | 42.4 | | |
| Durotak 2207 | | | 42.4 | |
| Silicone Adhesive | | | | 42.4 |

To prepare a transdermal patch containing synthetic cannabidiol, all of the components from Table 6, with the exception of the CBD, were mixed together with stirring for 18 hours. Next, the CBD was added 30 minutes before spreading the formulation. The formulation was spread using a commercial benchtop spreader. Specifically, the formulation matrix is evenly spread onto an 8×14 inch sheet of release liner (such as 3M 9744) to a thickness of 0.5 mm. The sheet is then place in an oven at 100° F. for one hour to evaporate off the ethyl acetate and ethanol adhesive solvent. An opaque backing membrane (such as 3M 9730 NR film) with low permeability to oxygen, for inhibition of photo and oxidative degradation, is then carefully applied to the sheet by hand to avoid formation of bubbles and voids. A circular die (1.5 inches diameter) was used to cut patches (7 cm$^2$) for subsequent studies.

The general procedure for flux measurements of transdermal formulations in the examples above was as follows. The human cadaver skin, stored at −80° C., was thawed at room temperature in PBS, and visually inspected for defects before use. Transdermal flux was measured using standard Franz diffusion cells composed of a cylindrical donor compartment and a separate water jacketed cylindrical receptor compartment with the volume of 13 mL. The human cadaver skin was clamped between the two compartments with the dermis side facing toward the receptor compartment. The general procedure for flux measurement of the transdermal adhesive patch is as follows. The release liner is peeled off the patch and the adhesive surface is applied to a piece of human cadaver skin. The transdermal patch was adhered to the skin with the patch on the side of the skin in contact with the donor compartment. The receptor compartment was filled with receptor medium, held at constant temperature, and constantly stirred to collect the CBD as it diffuses from the adhered patch, through the skin and into receptor compartment. It was confirmed that the receptor fluid was always in contact with the skin. The receptor compartment was emptied at 24 hour intervals for assay of CBD and replaced with fresh receptor solution. In order to maintain the sink condition in receptor compartment, the CBD concentration in the receptor compartment was maintained at less than 10% of its solubility. The experimental conditions are the same as provided in Table 2 of Example 15.

Example 17

Synthetic cannabidiol (CBD) formulations for transdermal delivery ((Formulation Nos. 047-055) were prepared by mixing ingredients as shown in Table 7:

TABLE 7

Transdermal Synthetic Cannabidiol formulations

| Excipients | CBD 047 | CBD 048 | CBD 049 | CBD 050 | CBD 051 | CBD 052 | CBD 053 | CBD 054 | CBD 055 |
|---|---|---|---|---|---|---|---|---|---|
| CBD | 4.84% | 4.98% | 4.73% | 4.99% | 4.87% | 4.89% | 5.04% | 4.83% | 5.00% |
| DUROTAK 2516 | 95.16% | — | — | — | — | — | — | — | — |
| DUROTAK 9301 | — | 95.02% | — | — | — | — | — | — | — |
| DUROTAK 2287 | — | — | 95.27% | — | — | — | — | — | — |
| DUROTAK 2054 | — | — | — | 95.01% | — | — | — | — | — |
| DUROTAK 2852 | — | — | — | — | 95.13% | — | — | — | — |
| DUROTAK 2074 | — | — | — | — | — | 95.11% | — | — | — |
| DUROTAK 2194 | — | — | — | — | — | — | 94.96% | — | — |
| BIO-PSA 4501 | — | — | — | — | — | — | — | 95.17% | — |
| BIO-PSA 4201 | — | — | — | — | — | — | — | — | 95.00% |

The above ingredients (Table 7) are blended by stirring for 18 hours and then, using a commercial benchtop spreader, the matrix is evenly spread onto an 8×14 inch sheet of release liner (such as 3M 9744) to a thickness of 0.5 mm. The sheet is then place in an oven at 86 F for 120 min to evaporate off the ethyl acetate adhesive solvent. An opaque backing membrane (such as 3M 9730 NR film) with low permeability to oxygen to inhibit photo and oxidative degradation, is then carefully applied by hand to avoid formation of bubbles and voids. A circular die (1.5 inches diameter) is used to cut patches (1.76 sqcm) for subsequent studies. After drying, the drug adhesive matrix has a surface density of 2-30 mg/sqcm, containing CBD in 5% w/w.

The prepared formulations where then subjected to a release study as follows: After weighing the patches (n=3), the release liner was removed, and the patches were placed in 20 ml scintillation vials with 15 ml of receiving media. The receiving media was PBS solution of pH 7.4 with 0.5% Brij(O)20. Vials were placed on the roller overnight at 20 RPM. Samples were withdrawn every 24 hours, up to 72 hours, and media was fully replaced each time. Samples were then run in the HPLC in order to determine the % release of CBD from the different formulations.

The prepared formulations also analyze for the uniformity of drug content. The patches (n=3) were weight out for each formulation, the release liner was removed, and the patches (including the release liner) were placed in 20 ml scintillation vials with 15 ml of solution IPA:Ethanol (I90proof) (50:50). The vials were then placed on the roller at 20 RPM and left overnight. Samples were withdrawn from each vial and analyzed on the HPLC in order to determine the drug content of each formulation.

TABLE 8

| Experimental Condition for In-vitro Permeability testing | |
| --- | --- |
| Receiving Media | PBS (pH 7.4) + 0.5% Brij-O(20) + 0.01% Sodium Azide |
| Receiving Media Volume (mL) | 15 |
| Sample Volume (mL) | 15 |
| Sampling Interval (hr) | 24, 48 |
| Diffusion area (sqcm) | 1.76 |

% Release of CBD through the matrix system was measured for a minimum period of 48 Hrs (2 days) and results of the % release are provided in Table 9.

TABLE 9

| | % CBD Release Results | | | | | | | | |
| --- | --- | --- | --- | --- | --- | --- | --- | --- | --- |
| | CBD 047 | CBD 048 | CBD 049 | CBD 050 | CBD 051 | CBD 052 | CBD 053 | CBD 054 | CBD 055 |
| Av. % Release at 24 hours | 26 (3) | 19 (7) | 20 (7) | 40 (2) | 23 (8) | 35 (12) | 37 (6) | 93 (2) | Did not solubilize the CBD 98% (0.05) |
| Av. % Release at 48 hours | 18 (7) | 6 (12) | 13 (13) | 22 (1) | 13 (9) | 12 (1) | 22 (5) | 2 (2) | |
| % Release 0-48 hours (cumulative) | 44 | 15 | 33 | 62 | 36 | 47 | 59 | 95 | |
| % CBD from extraction (STD) | 104 (2) | 100 (1) | 100 (5) | 102 (1) | 103 (6) | 96 (15) | 104 (4) | 107 | |

Drug content study showed that the % recover of CBD in extraction is Between 96-107% for all the manufactured formulations. Furthermore, the release study showed that the silicone adhesive 4501 showed more than 90% release within first 24 hrs. Based on the release profile following are the best adhesive for CBD formulation: BIOPSA-4501 2054=2194>2074>2516>2852=2287>9301.

Release studies indicate that the functional group and crosslinker affect the CBD release from acrylic adhesive. According to current study, acrylic adhesive containing —COOOH functional group with crosslinker showed the maximum release of CBD from all the acrylic adhesive patches.

Example 18

Additional synthetic Cannabidiol (CBD) formulations for transdermal delivery (Formulation Nos. 057 through 064) were prepared by mixing ingredients as shown in Table 10:

TABLE 10

| Transdermal Synthetic Cannabidiol formulation no. 057 to 064 | | | | | | | | |
| --- | --- | --- | --- | --- | --- | --- | --- | --- |
| Excipients | CBD 057 | CBD 058 | CBD 059 | CBD 060 | CBD 061 | CBD 062 | CBD 063 | CBD 064 |
| CBD | 5.0% | 5.0% | 5.0% | 4.9% | 4.8% | 4.8% | 4.9% | 4.8% |
| BIO-PSA 4501 | 95.0% | 84.6% | 84.5% | 85.0% | 83.3% | 89.7% | 86.9% | 89.6% |
| IPM | — | 10.4% | — | — | — | — | — | — |
| IPP | — | — | 10.5% | — | — | — | — | — |
| Oleic Acid | — | — | — | 10.1% | — | — | — | — |
| Transcutol P | — | — | — | — | 11.9% | — | — | — |
| Brij O20 | — | — | — | — | — | 5.5% | — | — |

TABLE 10-continued

Transdermal Synthetic Cannabidiol formulation no. 057 to 064

| Excipients | CBD 057 | CBD 058 | CBD 059 | CBD 060 | CBD 061 | CBD 062 | CBD 063 | CBD 064 |
|---|---|---|---|---|---|---|---|---|
| Poloxamer 124 | — | — | — | — | — | — | 8.2% | — |
| PGML | — | — | — | — | — | — | — | 5.6% |

Synthetic Cannabidiol formulations for transdermal delivery (057-064) were prepared by the same procedure described in Example 17.

The prepared transdermal formulations were then subjected to a flux measurement test as follows. Human cadaver skin, stored at −80° C., was thawed at room temperature in phosphate buffered saline (PBS), and visually inspected for defects before using in the study. Transdermal flux was then measured using standard Franz diffusion cells composed of a cylindrical donor compartment and a separate water jacketed cylindrical receptor compartment with the volume of 13 mL. The human cadaver skin was clamped between the two compartments with the dermis side facing toward the receptor compartment. The donor compartment was filled with the transdermal CBD formulations prepared as described above. The receptor compartment was filled with receptor medium, held at constant temperature, and constantly stirred to collect the CBD as it diffuses through the skin and into receptor compartment. It is important to confirm that the receptor fluid is always in contact with the skin. The receptor compartment was emptied at 24 hr intervals for assay of CBD and replaced with fresh receptor solution. In order to maintain the sink condition in receptor compartment, it is important to keep the CBD concentration in receptor compartment less than 10% of its solubility. The experimental conditions are provided in Table 11:

TABLE 11

| Experimental Condition for In-vitro Permeability testing | |
|---|---|
| Receiving Media | De-ionized water + 0.5% Brij-O(20) + 0.01% Sodium Azide |
| Receiving Media Volume (mL) | 13 |
| Sample Volume (mL) | 13 |
| Sampling Interval (hr) | 24, 48, 72, 96 |
| Franz-cell diffusion area (sqcm) | 1.76 |
| Membrane Type | Human Cadaver Skin |

Flux of CBD through the human cadaver skin was measured for a minimum period of 96 Hrs (4 days) and results of the flux measurement are provided in Table 12.

Upon completion of the flux study, the used patches were carefully removed and extract the CBD from the use patches using IPA:Ethanol (50:50). The human cadaver skin was also soaked in IPA:Ethanol (50:50), in order to extract the CBD from it. The samples were analyzed using HPLC. The data in Table 12 showed the amount of CBD present in the skin and the left-over patches.

TABLE 12

| | CBD Flux Results | | | | | | | |
|---|---|---|---|---|---|---|---|---|
| Excipients | CBD 057 | CBD 058 | CBD 059 | CBD 060 | CBD 061 | CBD 062 | CBD 063 | CBD 064 |
| Av. cumulative amount permeated at 96 hrs (μg) | 52 | 31 | 16 | 120 | 86 | BLLQ | BLLQ | 53 |
| Av. flux 24-96 hrs (μg/hr/sqcm) | 0.41 | 0.37 | 0.37 | 0.69 | 0.51 | BLLQ | BLLQ | 0.42 |
| Peak flux (μg/hr/sqcm) | 0.44 | 0.38 | 0.38 | 0.82 | 0.60 | BLLQ | BLLQ | 0.44 |
| Time to peak flux (hrs) | 72 | 72 | 72 | 72 | 72 | 0 | 0 | 72 |
| Av. CBD Amount in patch (mg) | 1.57 | Did not Determine | | 1.14 | 2.26 | 1.81 | 1.88 | 1.56 |
| Av. CBD Amount in skin (mg) | 0.01 | | | 0.59 | 0.13 | 0.54 | 0.24 | 0.10 |

Example 19

The effect of gelling agents and their concentration on the permeation of CBD through human cadaver skin. CBD gel formulation can be gelled by gelling agents including but not limited to, natural polymers such as natural polymers, polysaccharides and its derivatives such as but not limited to (agar, alginic acid and derivatives, *cassia* tora, collagen, gelatin, gellum gum, guar gum, pectin, potassium or sodium carrageenan, tragacanth, xanthum gum, copal, starch, chitosan, resin etc.), synthetic polymers and its derivatives such as without any limitation to carboxyvinyl polymers or carbomers (carbopol 940, carbopol 934, carbopol 971), polyethylene and its co-polymers etc. clays such as silicate etc. polyvinyl alcohol, polyacrylamide, polyvinyl pyrrolidone homopolymer and polyvinyl pyyrolidone copolymers (PVP, Poloxamer, PVPK-30, PVPK-90,), acrylic acid its ester, polyacrylate copolymers, isobutylene, ethylene vinyl acetate copolymers, natural rubbers, synthetic rubbers such as styrene-diene copolymers, styrene-butadiene block copolymers, isoprene block copolymers, acrylonitrile butadiene rubber, butyl rubber or neoprene rubber, as well as pressure sensitive adhesive based on silicone, or "hot-melt adhesive". In addition, other than human cadaver skin, CBD can be evaluated with other artificial membranes including but not limited to cellulose membrane, silicone membranes (polydimethylsiloxane), liposome coated membranes, solid-supported liquid membranes, lecithin organogel membrane and other. Besides the gel formulation of CBD, other dosage forms including but not limited to ointment, creams, emulsion, liposomes, etc. may be used.

Example 20

The effect of enhancers or solubilizers on the flux of CBD through human cadaver skin was evaluated. The desire optimum composition of CBD gel formulation contained dimethylsulfoxide (DMSO), dimethylisosorbide (DMI), Lactic acid, Tween-20, highly purified diethylene glycol monoethyl ether (Transcutol P), dipropylene glycol, polyethylene glycol-400, propylene glycol (PG), Hexylene Glycol (HG), Lauroglycol-90, Soluplus® (polyvinyl caprolactam-polyvinyl acetate-polyethylene glycol graft co-polymer). Apart from above mentioned enhancers and/or solubilizers, the CBD transdermal delivery can be influenced by enhancers and/or solubilizers including but not limited water, sulfoxides, and similar chemicals such as but not limited to (dimethylsulfoxide, dimethylacetamide, dimethylformamide, decylmethylsulfoxide, dimethylisosorbide etc), azone, pyrrolidones such as but not limited to (N-methyl-2-pyrrolidone, 2-pyrrolidon etc), esters such as but not limited to (Propylene glycol monolaurate, butyl ethanoate, ethyl ethanoate, isopropyl myristate, isopropyl palmitate, methyl ethanoate, decyl oleate, glycerol monooleate, glycerol monolaurate, lauryl laurate etc), fatty acids such as but not limited to (capric acid, caprylic acid, lauric acid, oleic acid, myristic acid, linoleic acid, stearic acid, palmitic acid etc), alcohols, fatty alcohols and glycols such as but not limited to (oleyl alcohol, nathanol, dodecanol, propylene glycol, glycerol etc), ethers such as but not limited to (diethylene glycol monoethyl ether), urea, polyoxyethylene fatty alcohol ethers, polyoxyethylene fatty acid esters, esters of fatty alcohols, esters of long chain fatty acids with methyl, ethyl or isopropyl alcohol, esters of fatty alcohols with acetic acid, lactic acid, as well as oleic acid diethanolamine, essential oils, terpene and terpenoids such as but not limited to (terpineol, limonene, thymol, cineole etc), surfactant type enhancers (polysorbate 80, polysorbate 20 etc.), liposomes, niosomes, transferomes, ethanosomes, polysorbate such as but not limited to (polysorbate 20, polysorbate 40, polysorbate 60, polysorbate 80 etc), span such as but not limited to (span 80, span 20 etc), surfactants such as (anionic, cationic, nonionic and amphoteric), propylene glycol monocaprylate type I, propylene glycol monocaprylate type II, propylene glycol dicaprylate, medium chain triglycerides, propylene glycol monolaurate type II, linoleoyl polyoxyl-6 glycerides, Caprylic glyceride, oleoyl-polyoxyl-6-glycerides, lauroyl polyoxyl-6-gylcerides, polyglyceryl-3-dioleate, diethylene glycol monoethyl ether, propylene glycol monolaurate type I etc, cyclodextrins, polyhydric alcohol, especially 1,2-propanediol, butanediol, glycerine, polyethylene glycol (m.w. 100 and higher), Dimethyl Sulfoxide, Dimethyl Isosorbide, tetrahydrofurfuryl alcohol, diethyl tolumide, monoisopropylidene glycerine and others Solubilizers, surfactants, emulsifying agents, dispersing agents and similar compounds or chemicals known to those skilled in the art can be used either alone or in combination thereof

Example 21

Oral bioavailability of CBD is only 13-19%. For our calculation purpose, We took an average bioavailability of 15%17. So, the actual dose delivering to patient upon oral delivery is described in Table 13.

TABLE 13

Theoretical dose required from Transdermal Dosage form.

| Oral Dose | Transdermal Dose range (mg/day) |
|---|---|
| 6.2 mg/day | 0.93 |
| 62 mg/day | 9.3 |

Flux Required=Dose/Surface area
=0.93 mg/day/surface area
=930 ug/24 hr/50 sqcm
=0.78 ug/sqcm/hr So, 50 sqcm patch with 0.78 ug/sqcm/hr flux will deliver 0.93 mg of drug in one day through transdermal route which is equivalent to 6.2 mg/day oral dose. As we know that 6.2 mg/day dose is very effective to reduce knee-joint swelling. The current formulation can deliver required amount of CBD to reduce the arthritis pain.

Some research article showed oral bioavailability of CBD is in the range of 5-6%[17,18], which indicates that it might reduce patch size based on first-in-human bioavailability data.

Example 22

Patent application US2005/0266061 (Stinchcomb et al.) and Challapalli et. al. (Prasad V. N Challapalli, Audra L Stinchcomb. In vitro experiment optimization for measuring tetrahydrocannabinol skin permeation. International Journal of Pharmaceutics. Volume 241, Issue 2, 25 Jul. 2002, Pages 329-339) showed that naturally derived delta-9-THC has a skin permeability of 20 µg in 96 hrs. with 6% Brij O20. Furthermore, the same previous research also showed that THC has the highest permeability through the human cadaver skin when 6% of BRIJ® O20 is used in the receiving media to improve the solubility of THC in receiving media. (See FIG. 1 of US2005/0266061).

Formulations comprising synthetic THC or botanical extract THC were made and tested by applying the formulations to the donor side of Franz diffusion cells partitioned by a piece of human cadaver skin. A practical means to investigate transdermal formulations is to use a Franz diffusion cell wherein a piece skin, typically human cadaver skin obtained from a tissue bank, is clamped between a donor and receptor compartment. Drugs applied to the donor side can only reach the receptor side by diffusion through the skin. Thus, the rate of flux of the drug can be measured in response to various formulations applied to the donor side.

The formulations comprising synthetic THC or botanical extract THC were prepared as set forth in Table 14 below, which also reports the results of the flux study.

TABLE 14

| Formulation | Synthetic THC Formula | Literature Formula (US2005/0266061 A1) |
| --- | --- | --- |
| THC | 0.63% | 0.85% |
| Ethanol | 13.71% | 3.81% |
| Propylene Glycol (PG) | 77.10% | 85.80% |
| Water | 8.57% | 9.5% |
| Cumulative Amount of THC delivered through the Human Cadaver skin in 96 hrs. (ug) | 112 | 20 |
| Receiving Media | 0.5% Brij O20 | 6% Brij O20 |

The data in Table 14 show that the Synthetic version of delta-9-THC has more permeability than the naturally derived delta-9-THC. These data are unexpected, novel and not reported by any of the publications or patent applications. The reason for this improvement could be the purity of the API as compared to naturally derived API.

Example 23

Formulation comprising synthetic THC were made and the flux of synthetic THC through the human cadaver skin was measured for a period of up to 168 Hrs (7 days) and results of the flux measurement are provided in Table 15.

TABLE 15

Transdermal Matrix Formula

| Excipients (%W/W) | Formulation A | Formulation B |
| --- | --- | --- |
| Synthetic THC | 5 | 5 |
| PG | 12 | 12 |
| Oleic Acid | 4 | 10 |
| Bio PSA 4202 | 80 | 75 |
| Avg Flux Profile (ug/sqcm/hr) | | |
| Avg Flux 0-24 Hrs | 0 | 0 |
| Avg Flux 24-48 Hrs | 0 | 0 |
| Avg Flux 48-72 Hrs | 0 | 0.64 (100) |
| Avg Flux 72-96 Hrs | 1.08 (12.4) | 1.26 (26.7) |
| Avg Flux 96-120 Hrs | 0.93 (12.4) | 1.04 (16.8) |
| Avg Flux 120-144 Hrs | 1.04 (13.8) | 1.15 (16.4) |
| Avg Flux 144-168 Hrs | 0.78 (50.4) | 1.02 (14.9) |
| Avg Flux 0-168 Hrs | 0.55 (18.9) | 0.73 (28.9) |

In addition, it was found that the flux profile can be improved by using silicone dioxide, and other polymers to increase the drug concentration.

REFERENCES

1. Bruni, N. et. al., "Cannabinoid Delivery Systems for Pain and Inflammation Treatment", Molecules, 2018, 23(10), 2478-
2. Jensen, M. P.; Chodroff, M. J.; Dworkin, R. H., "The impact of neuropathic pain on health-related quality of life: Review and Implication", Neurology, 2007, 68, 1178-182
3. Di Marzo, V.; Bifulco, M.; De Petrocellis, L., "The Endocannabinoid system and its therapeutic exploitation" Nature review drug discover, 2004, 3, 771-784
4. Mehmedic Z., et. al., "Potency trends of delta-9-THC and other cannabinoids in confiscated *cannabis* preparation from 1993 to 2008", J. Forensic Sci, 2010, 5, 1209-17
5. Svizenska, I.; Dubovy, P.; Sulcova A., "Cannabinoid receptors 1 and 2 (CB1 and CB2), their distribution, ligands an functional involvement in central nervous system structure-A short review", Pharmacol Biochem Behav., 2008, 90(4), 501-511
6. Fukuda S. et al., "Cannabinoid receptor 2 as a potential therapeutic target in rheumatoid arthritis", BMC Musculoskelet Disord., 2014, 12, 15-275
7. Ligresti, A.; Petrocellis, L. D.; Di Marzo, V., "From Phytocannabinoids to cannabinoid receptors and Endocannabinoids: Pleiotropic physiological and Pathological Roles through Complex Pharmacology", Physio Rev., 96(4), 1593-659
8. Malfait, A. M. et. al., "The nonpsychoactive *cannabis* constituent cannabidiol is an oral anti-arthritic therapeutic in murine collagen-induced arthritis" Proc Natl Acad Sci USA, 2000, 97(17), 9561-9566
9. Akopian A. et. al., "Cannabinoids desensitize capsaicin and mustard oil responses in sensory neuron via TRPA1 activation", Journal of Neuroscience, 2008, 28(5), 1064-75
10. Schuelert, N.; McDougall, J. J., "Cannabinoid-mediated antinociception is enhanced in rat osteoarthritic knees", Arthritis Rehum., 2008, 58(1), 145-53
11. Robles, E. M. S.; Arias A. B.; Fontelles, M. M., "Cannabinoids and muscular pain. Effectiveness of the local administration in rat", Eur. J. Pain, 2012, 16(8), 1116-27
12. Correa F. et. al., "A role of CB2 receptors in anandamide signaling pathways involved in the regulation of IL-12 and IL-23 in microglial cells", Biochem Pharmacol., 2009, 77(1), 86-100
13. Cheng, Y.; Hitchcock, S. A., "Targeting Cannabinoid agonist for inflammatory and neuropathic pain", Expert opinion Investig Drugs, 2007, 16(7), 951-65
14. Shang, Y.; Tang, Y., "The central cannabinoid receptor type-2 (CB2) and Chronic Pain", Int J. Neurosci., 127(9), 812-823
15. Richardson, D. et. al., "Characterisation of the cannabinoid receptor system in synovial tissue and fluid in patient with osteoarthritis and rheumatoid arthritis", Arthritis Res. Ther., 10(2), R43
16. Hammell, D. C., et. al., "Transdermal cannabidiol reduced inflammation and pain-related behaviors in a rat model of arthritis", Eur. J. Pain, 20(6), 936-48
17. Atsmon J., et. al. "Single-Dose Pharmacokinetics of oral Cannabidiol Following Administration of PTL101: A New Formulation Based on Geltain Matrix Pellets Technology", Clinical Pharmacology in Drug Development, 2018, 7(7), 751-758
18. Zhornitsky S., et. al., "Cannabidiol in Humans—The Quest for Therapeutic Targets", Pharmaceuticals (Basel), 2012, 5 (5), 529-552

While the invention has been described in detail and with reference to specific examples thereof, it will be apparent to one skilled in the art that various changes and modifications can be made therein without departing from the spirit and scope thereof.

What is claimed is:

1. A pharmaceutical composition comprising tetrahydrocannabinol (THC), in a dosage form for transdermal delivery wherein the pharmaceutical composition comprises:
   a concentration of THC selected from the group consisting of about 1%, about 2%, about 3%, about 4%, about 5%, about 6%, about 7%, about 8%, about 9%, about 10%, about 11%, about 12%, about 13%, about 14%, and about 15% w/w;
   about 5% to about 20% w/w of a solvent comprising propylene glycol;
   about 1% to about 20% w/w of a penetration enhancer comprising oleic acid;
   about 0.1% to about 0.7% w/w of butylated hydroxytoluene;
   about 2% to about 15% w/w of at least one suspending agent comprising silicon dioxide;
   about 0.1% to about 20% w/w of polyvinylpyrrolidone; and
   about 50% to about 80% w/w of a silicone pressure sensitive adhesive,
   wherein the pH of the composition is maintained at approximately 4.0 to 8.0, wherein the pharmaceutical composition is in the form of a transdermal matrix patch,
   further wherein the pharmaceutical composition provides a constant rate of delivery of the active components of the transdermal matrix patch in a therapeutic range in a patient over 7 days.

2. The pharmaceutical composition of claim 1 further comprising carriers or ingredients selected from the group consisting of gelling agents, polymers, emollients, skin irritation reducing agents, buffering agents, pH stabilizers, solubilizers, dispersing agents, stabilizers, plasticizers, surfactants, antioxidants, oxidants, and combinations thereof.

3. The pharmaceutical composition of claim 1 further comprising carriers or ingredients selected from the group consisting of gelling agents, polymers, emollients, skin irritation reducing agents, buffering agents, pH stabilizers, solubilizers, dispersing agents, stabilizers, plasticizers, surfactants, antioxidants, oxidants, and combinations thereof in the range of 0.01%-95% w/w or w/v.

4. The pharmaceutical composition of claim 1 which is formulated as a transdermal matrix patch formulation which can be administered in a dosage regimen selected from the group consisting of once in a week, once in about 8 to about 13 days, once in two weeks, once in about 15 days to about 30 days.

5. The pharmaceutical composition of claim 1 wherein said THC is produced by a synthetic route.

6. A method for the treatment of pain and/or inflammation comprising: selecting a patient in need of treatment of pain and/or inflammation; topically applying a pharmaceutical composition of claim 1, in a dosage form for transdermal delivery.

7. The method of claim 6, wherein the topical application of a transdermal patch for the treatment of pain and/or inflammation is selected from the group consisting of once in a day, once in two days, once in three days, once in four days, once in five days, once in six days, once in a week, once in ten days.

8. The method of claim 6 further providing a constant rate of delivery of the active components of the transdermal patch over a time period.

9. The method of claim 6 further providing a steady absorption rates of the active components of the transdermal patch over a time period.

10. The method of claim 6 further achieving a constant blood serum levels of the active components of the transdermal patch over a time period.

11. The method of claim 6 further achieving a reduced variability in dosage of the active components of the transdermal patches over a time period.

12. The method of claim 6 further providing a plasma concentration of the active components of the transdermal patch in a therapeutic range over a period of time.

13. The method of claim 6 wherein the topical application of a transdermal patch is for the treatment of pain and/or inflammation of indications selected from the group consisting of headaches, migraine, tension headaches, cluster headaches, acute pain, chronic pain, neuropathic pain, nociceptive pain, central pain, inflammatory pain, fibromyalgia, drug-induced neuropathic pain, causalgia, complex regional pain syndrome types I and II, and reflex sympathetic dystrophy (RSDS), pain and wasting associated with AIDS, arthritis and rheumatism, migraines, and muscle spasticity associated with multiple sclerosis and paralysis, Autism Spectrum Disorder (ASD) and Autism Spectrum Disorder (ASD) for Pediatric patients, pain and/or inflammation of patients with liver disease, pain and/or inflammation of patients with kidney disease, pain and/or inflammation for liver cancer patients, treating pain and/or inflammation for kidney cancer patients, pain and/or inflammation for cancer patients; Parkinson's Disease; pain and/or inflammation of patients with Parkinson's Disease, and combinations thereof.

14. A method for the treatment of Parkinson's Disease comprising: selecting a patient in need of treatment of Parkinson's Disease; topically applying a pharmaceutical composition of claim 1, in a dosage form for transdermal delivery.

15. The method of claim 6, wherein the topical application of a transdermal patch for the treatment of Parkinson's Disease is selected from the group consisting of once in a day, once in two days, once in three days, once in four days, once in five days, once in six days, once in a week, once in ten days.

16. The method of claim 6 further providing a constant rate of delivery of the active components of the transdermal patch over a time period.

17. The method of claim 6 further providing a steady absorption rate of the active components of the transdermal patch over a time period.

18. The method of claim 6 further achieving a constant blood serum level of the active components of the transdermal patch over a time period.

19. The method of claim 6 further achieving a reduced variability in dosage of the active components of the transdermal patches over a time period.

20. The method of claim 6 further providing a plasma concentration of the active components of the transdermal patch in a therapeutic range over a period of time.

21. The method of claim 6 wherein the topical application of a transdermal patch is for the treatment of pain and/or inflammation of patients with Parkinson's Disease.

* * * * *